United States Patent [19]
Olweus et al.

[11] Patent Number: 6,096,540
[45] Date of Patent: *Aug. 1, 2000

[54] DIFFERENTIATION OF GRANULOCYTIC AND MONOCYTIC PROGENITOR CELLS

[75] Inventors: Johanna Olweus; Fridtjof Lund-Johansen, both of Palo Alto; Peter Thompson, Danville, all of Calif.

[73] Assignee: Becton Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/724,725

[22] Filed: Sep. 30, 1996

[51] Int. Cl.$^7$ ............................. C12N 5/00; C12N 5/06; C12N 5/08
[52] U.S. Cl. ........................... 435/343; 435/325; 435/372
[58] Field of Search ..................................... 435/325, 372, 435/343

[56] References Cited

FOREIGN PATENT DOCUMENTS

| | | |
|---|---|---|
| WO 90/09400 | 8/1990 | WIPO . |
| WO 94/02016 | 2/1994 | WIPO . |
| 9512813 | 5/1995 | WIPO . |

OTHER PUBLICATIONS

Olweus et al. Blood 85: 2402–2413 (1995).
Zhang et al. Mol. Cell. Biol 14:373–381 (1994).
Gliniak et al. Cell 63: 1073–1083 (1990).

*Primary Examiner*—Christina Chan
*Assistant Examiner*—Gerald R. Ewoldt
*Attorney, Agent, or Firm*—Daniel M. Becker; Vicki S. Veenker; Fish & Neave

[57] ABSTRACT

The present invention demonstrates that M-CSF responsiveness and the M-CSFR expression can be used to discriminate monocytic and granulocytic cells within a population of cells which strongly expresses the CD34 antigen (CD34$^{hi}$). Briefly, the method comprises isolating phenotypically and functionally defined CD34$^+$ subsets, and staining with anti-M-CSFR monoclonal antibodies to measure expression on these primitive progenitors and cells committed to the granulocytic and monocytic lineages, based upon expression of M-CSFR. CD34$^{hi}$M-CSFR$^{hi}$ cells are highly clonogenic and approximately 70% of the colonies are CFU-M (monocytic), whereas less than 20% were CFU-G (granulocytic). In contrast, CD34$^{hi}$ cells that were positive for the granulo-monocytic marker CD64 and negative for the M-CSFR contained high frequencies of 91% pure CFU-Gs. After 60 h in culture, CD34$^{hi}$M-CSFR$^{hi}$ cells developed into distinct populations of M-CSFR$^{hi}$ and M-CSFR$^{lo}$ cells. These two populations gave rise almost exclusively to monocytes and granulocytes, respectively. This result demonstrates that M-CSF target specificity among human hematopoietic progenitor cells is determined by lineage-specific regulation of the M-CSFR and demonstrate that M-CSFR is a useful marker to discriminate CFU-Ms from CFU-Gs.

8 Claims, 15 Drawing Sheets

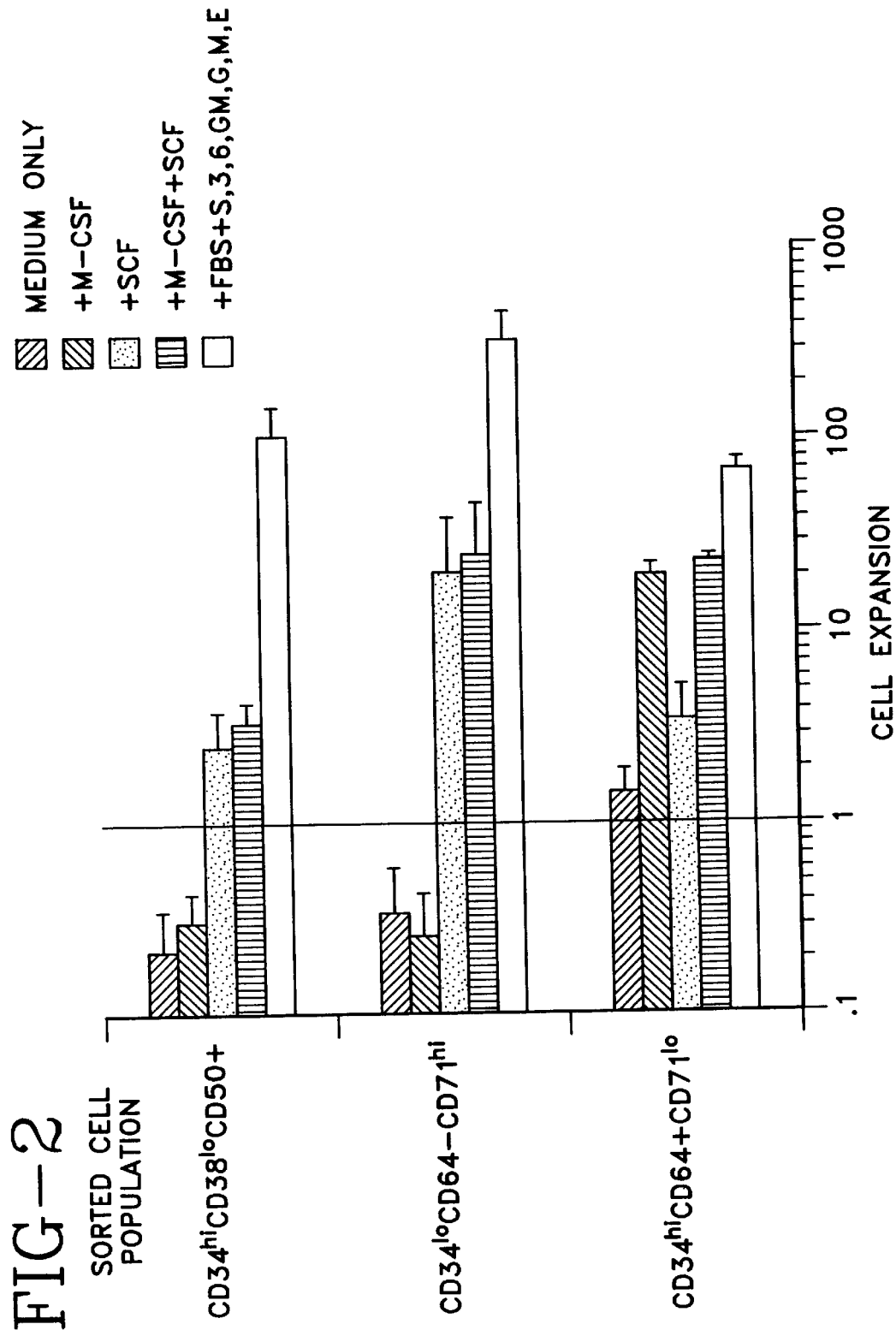

FIG-3A CD14 FITC
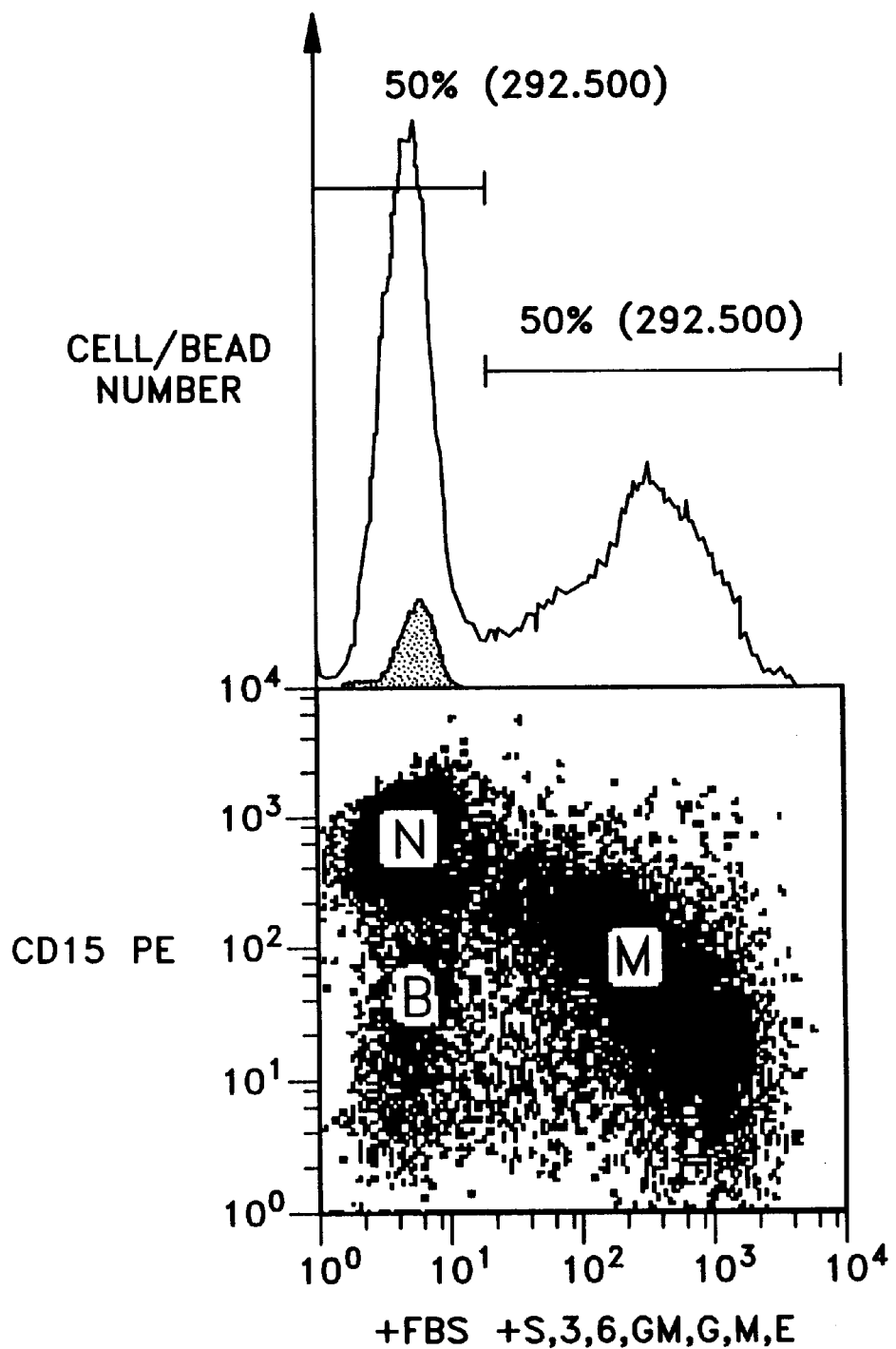

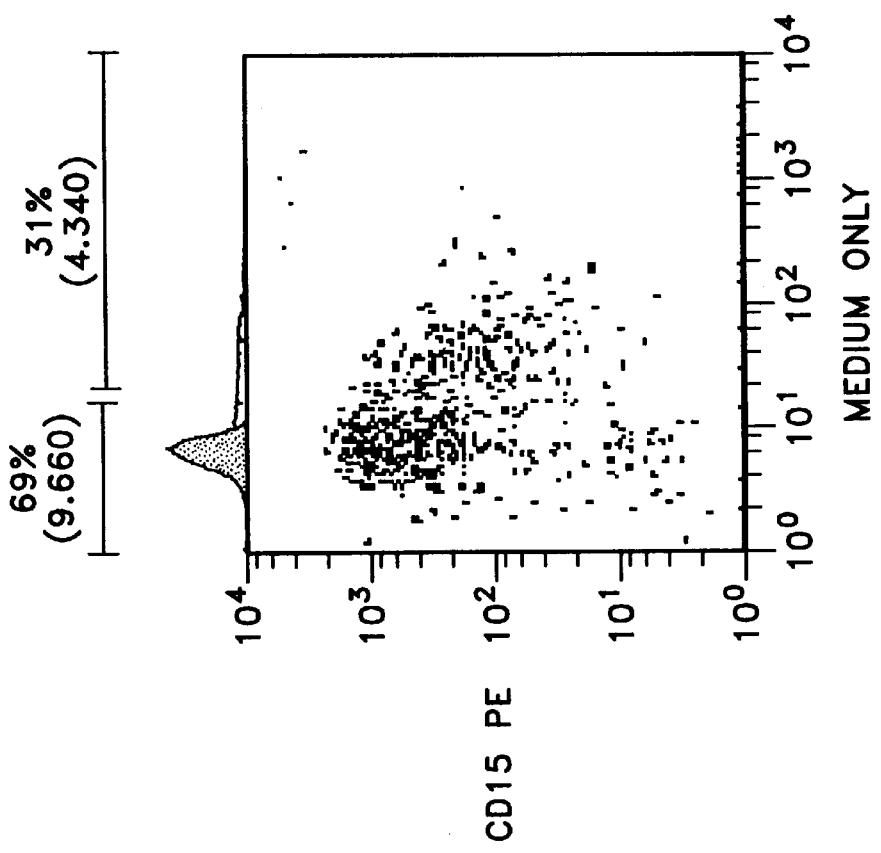
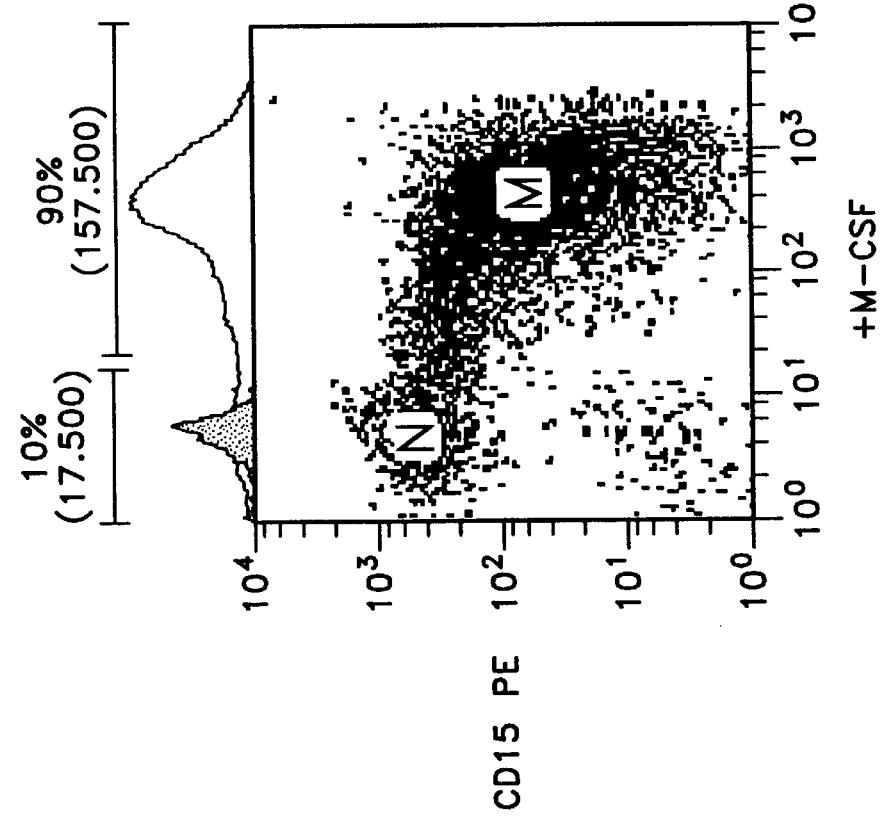
FIG-3B
FIG-3C

FIG-4A CD34+ CELLS
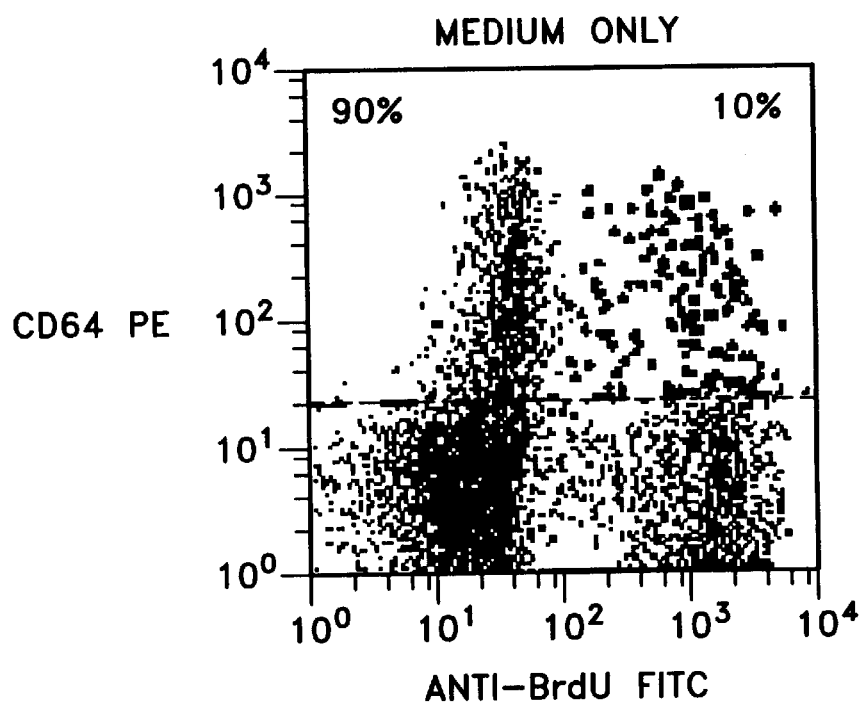
FIG-4B CD34+ CELLS
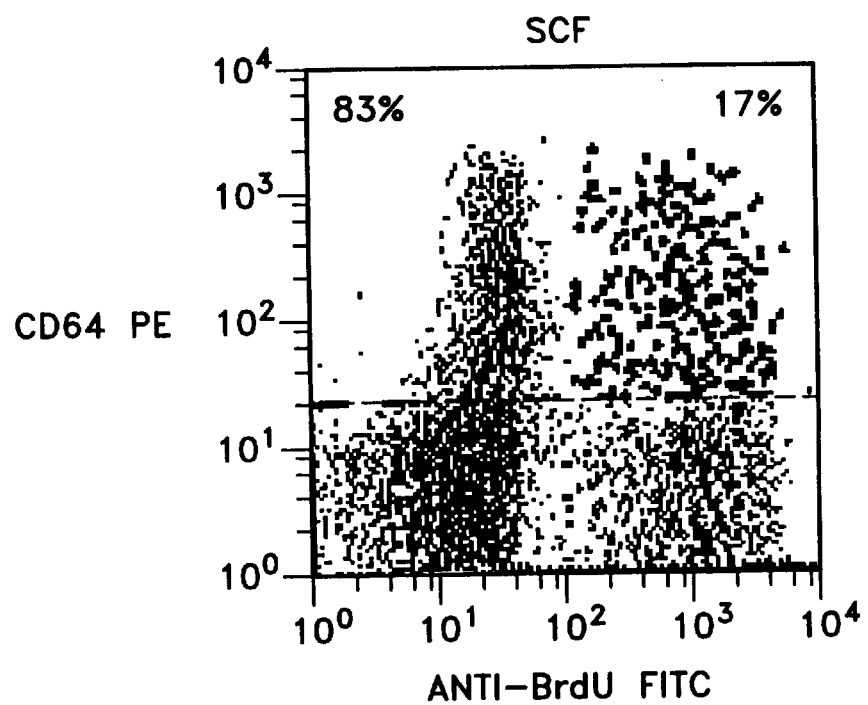

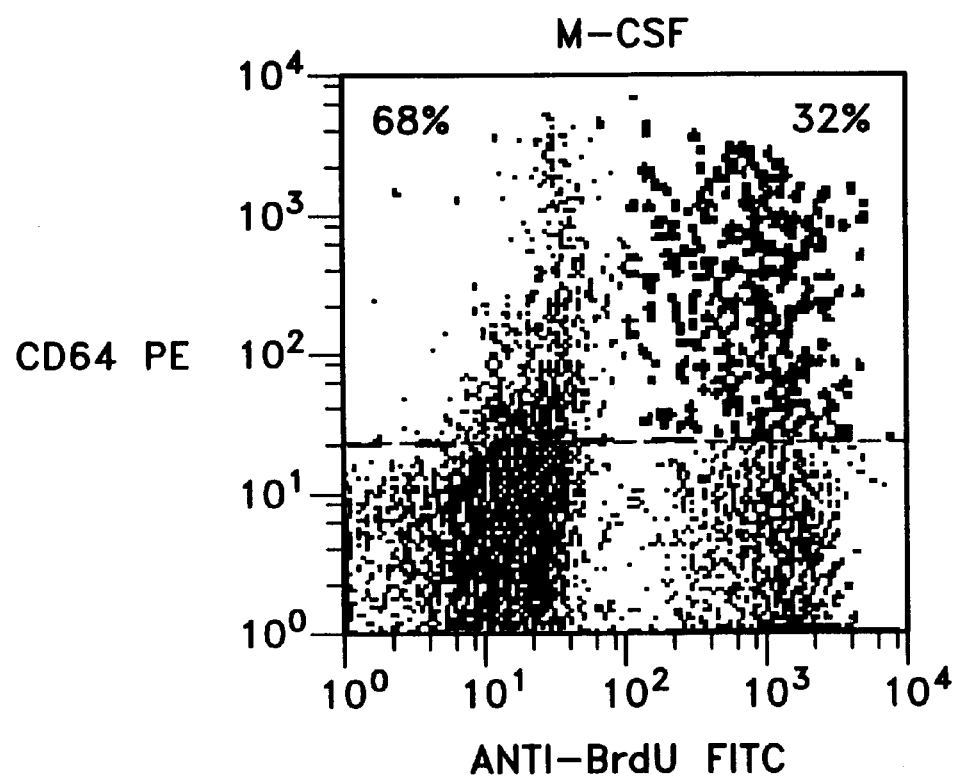
FIG-4C CD34+ CELLS

FIG-5A ALL CELLS
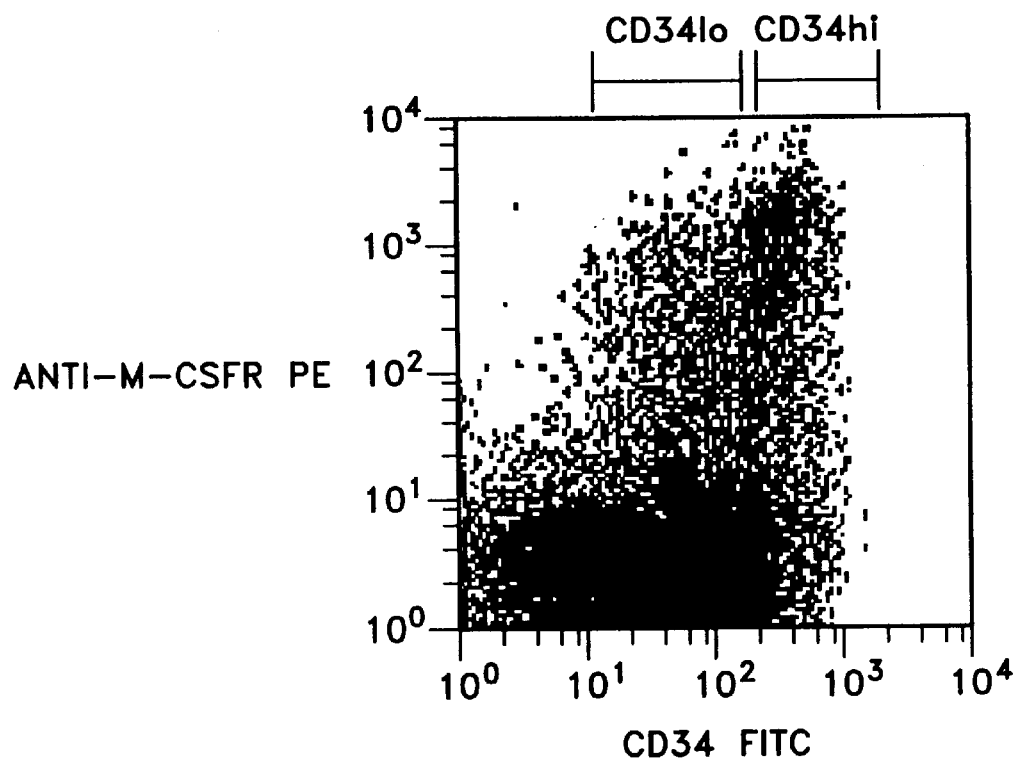
FIG-5B ALL CELLS
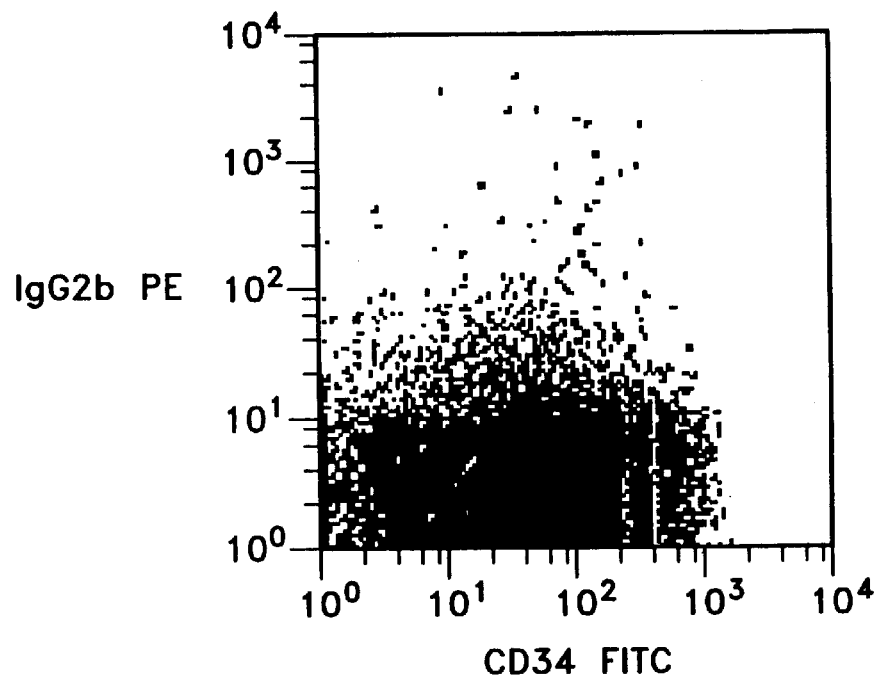

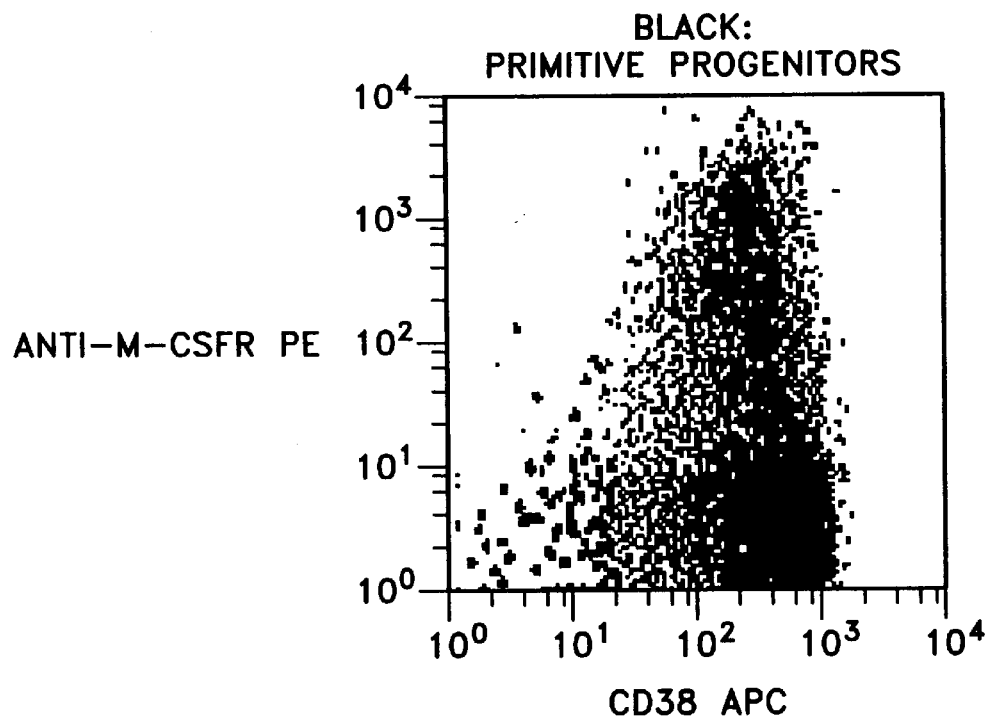
FIG-5C CD34+ CELLS
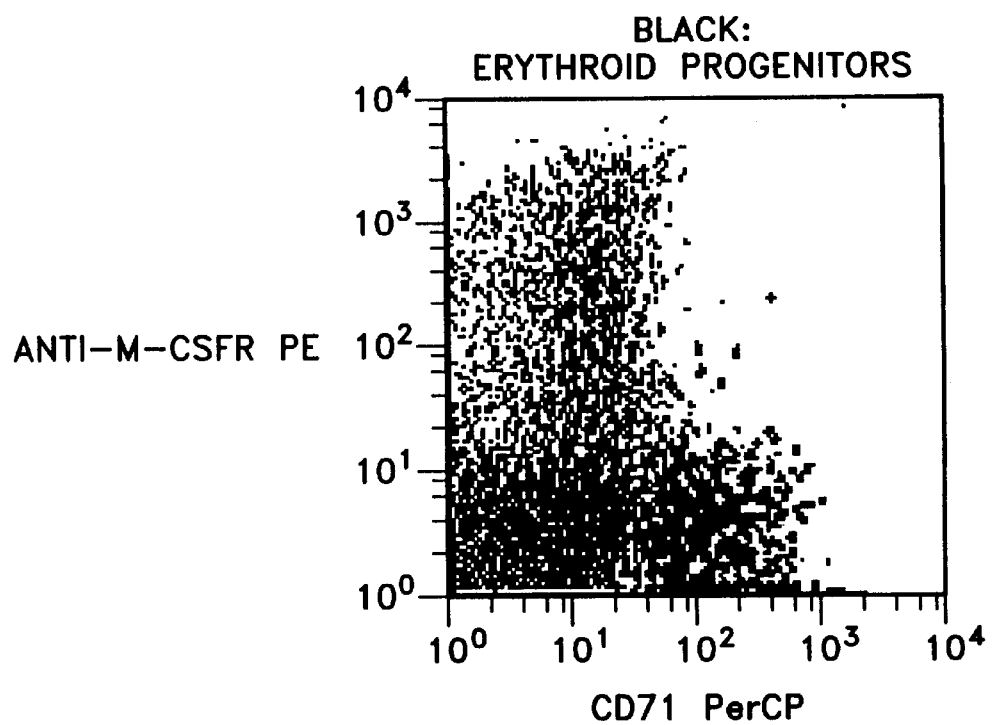
FIG-5D CD34+ CELLS

FIG-5E CD34+ CELLS
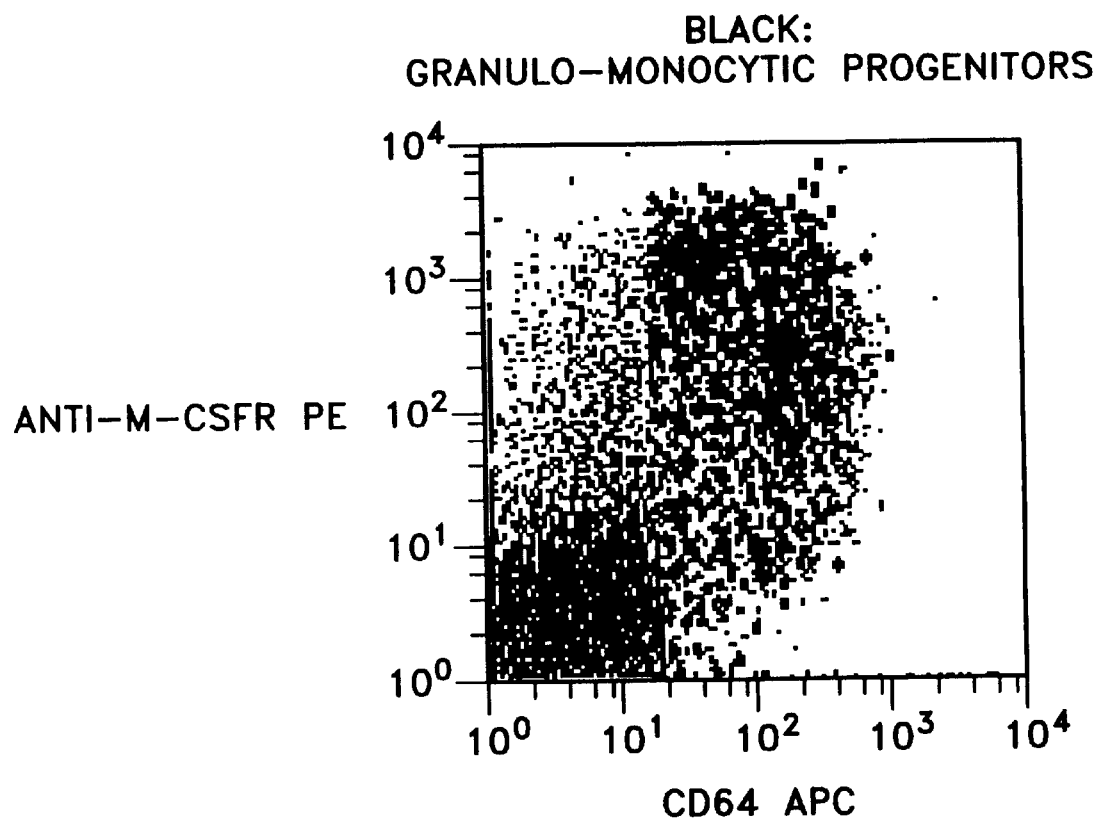

FIG-6A CD34^hl CELLS
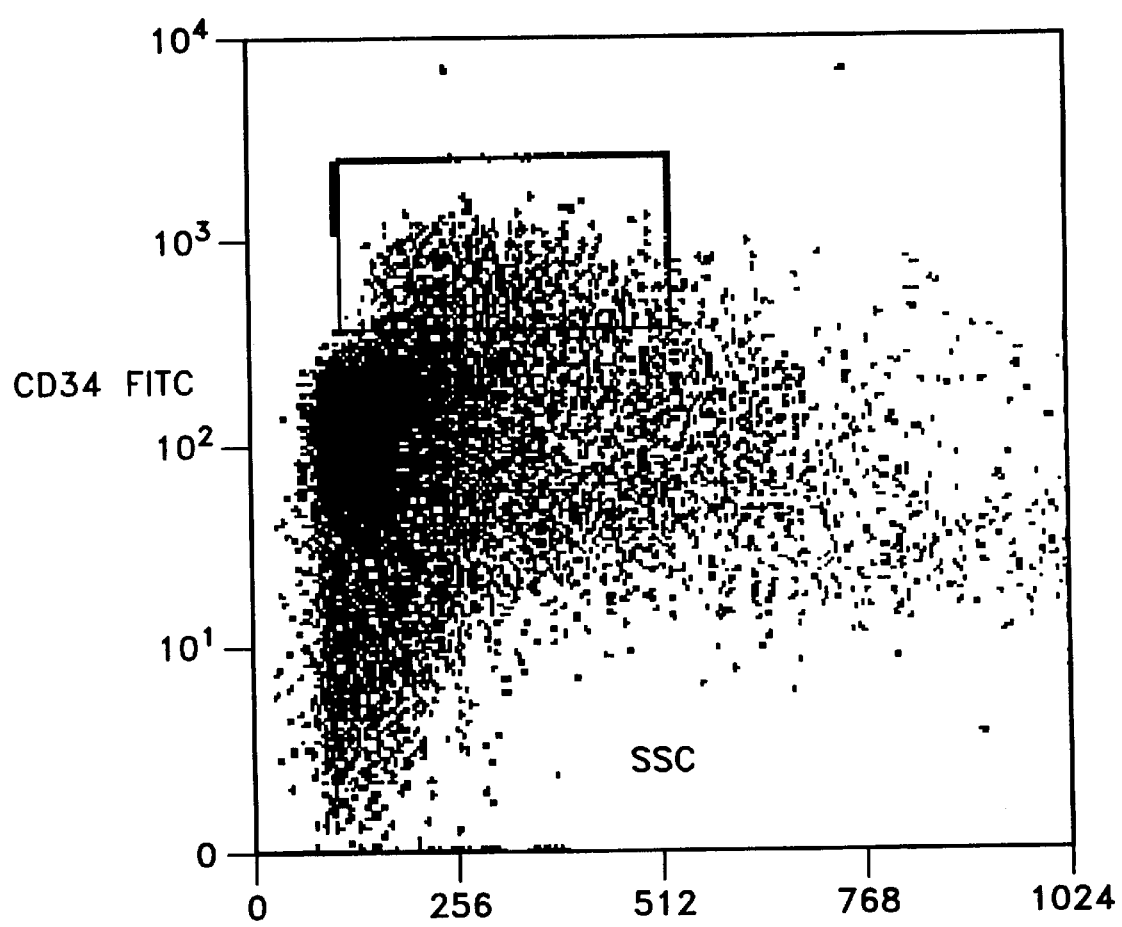

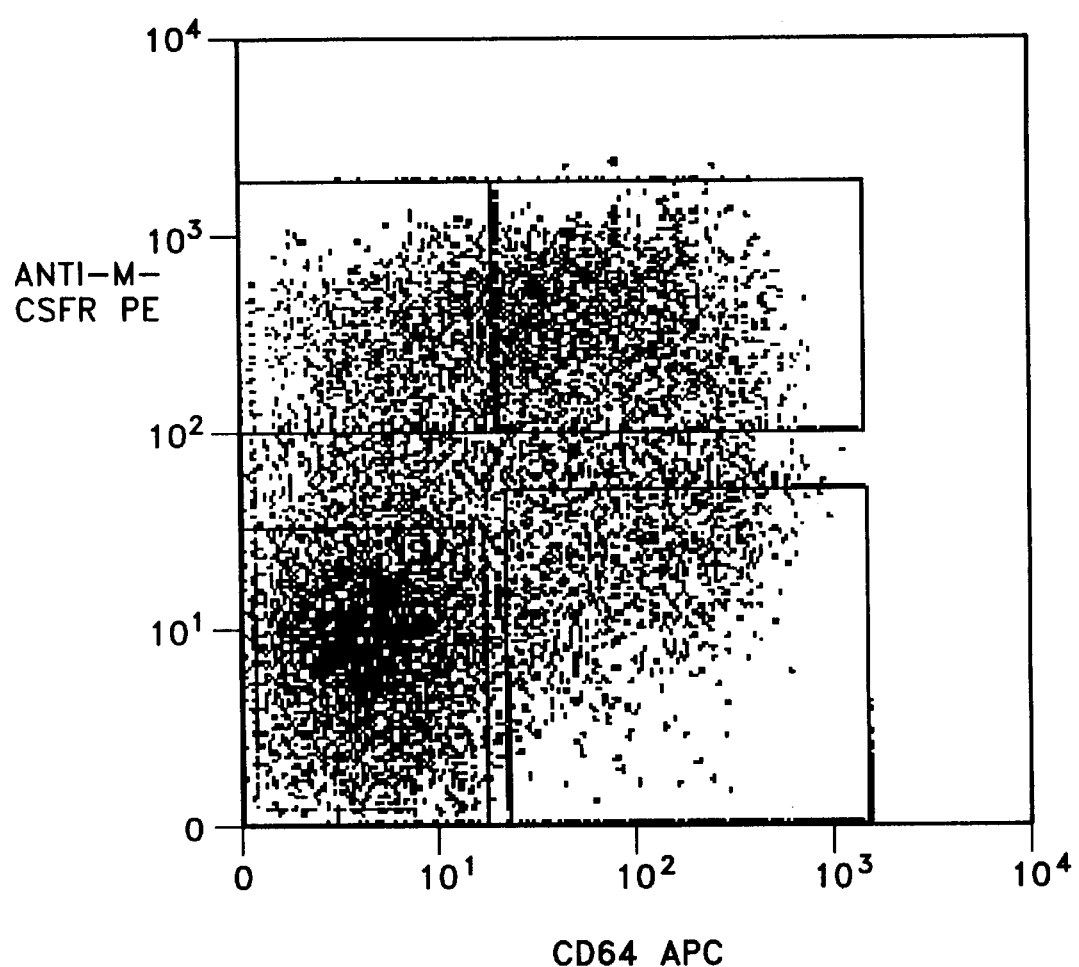
FIG-6B CD34^hi CELLS

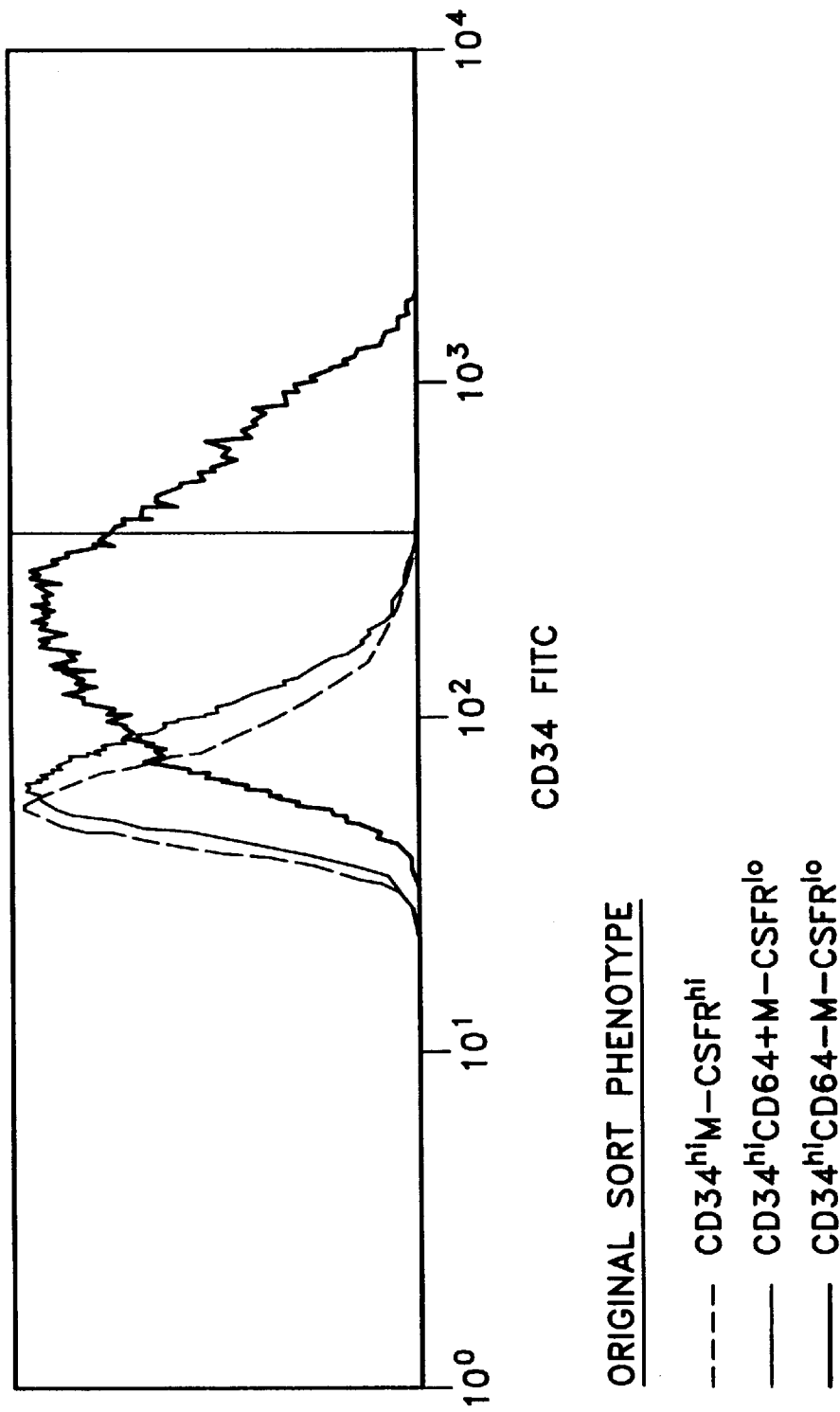

DIFFERENTIATION OF GRANULOCYTIC AND MONOCYTIC PROGENITOR CELLS

BACKGROUND OF INVENTION

During early hematopoietic development, multipotent stem cells proliferate and differentiate into lineage-committed progenitors. This process is currently poorly understood, and it is not known how differentiation and proliferation are regulated by extracellular factors. The ability to influence these events is, however, critical for ex vivo expansion and manipulation of hematopoietic progenitor cells. A better understanding of the early steps of hematopoiesis depends on a more precise definition of progenitor cell types as well as knowledge about molecules that are regulated during the transition from one stage of maturation to the next.

Subsets of hematopoietic progenitor cells respond differently to a large number of cytokines. For certain cytokines, differences in cellular responsiveness have been ascribed to changes in receptor expression during early progenitor cell differentiation. It has recently been demonstrated that the receptor for etythropoietin (EPO-R) is specifically expressed on cells that have undergone commitment to the erythroid lineage. This suggests that the receptor for a lineage-restricted cytokine may serve as an early marker of progenitor cell commitment. M-CSF is another cytokine with highly selective activity. Injection of M-CSF into non-human primates leads to an increase in the number of monocytes in peripheral blood, whereas no changes are observed in the number of other myeloid cells. Colonies formed when bone marrow cells are cultured in the presence of M-CSF alone contain predominantly monocytic cells. When added in combination with other cytokines, M-CSF stimulates the formation of high proliferative potential colonies (HPP-CFCs). This indicates that the ability to respond to M-CSF may be an early event in myeloid development.

The present invention demonstrates that M-CSF responsiveness and the M-CSFR expression can be used to discriminate monocytic and granulocytic cells within a population of cells which strongly expresses the CD34 antigen ($CD34^{hi}$). Briefly, the method comprises isolating phenotypically and functionally defined $CD34^+$ subsets, and staining with anti-M-CSFR monoclonal antibodies to measure expression on these primitive progenitors and cells committed to the granulocytic and monocytic lineages, based upon expression of M-CSFR. $CD34^{hi}$M-$CSFR^{hi}$ cells were highly clonogenic and approximately 70% of the colonies were CFU-M (monocytic), whereas less than 20% were CFU-G (granulocytic). In contrast, $CD34^{hi}$ cells that were positive for the granulo-monocytic marker CD64 and negative for the M-CSFR contained high frequencies of 91% pure CFU-Gs. After 60 h in culture, $CD34^{hi}$M-$CSFR^{hi}$ cells developed into distinct populations of M-$CSFR^{hi}$ and M-$CSFR^{lo}$ cells. These two populations gave rise almost exclusively to monocytes and granulocytes, respectively. This result demonstrates that M-CSF target specificity among human hematopoietic progenitor cells is determined by lineage-specific regulation of the M-CSFR and demonstrate that M-CSFR is a useful marker to discriminate CFU-Ms from CFU-Gs.

BRIEF DESCRIPTION OF FIGURES

FIG. 2 graphically depicts the effect of M-CSF on survival and proliferation of primitive and lineage-committed progenitor cells cultured in serum-free (SF) liquid medium for 5 days. The indicated cell populations were sorted as described in the legend to FIG. 1 and cultured in SF medium only or SF medium supplemented with M-CSF or SCF or both. Alternatively, the cells were cultured in medium containing 20% fetal bovine serum and SCF, IL-3, IL-6, GM-CSF, M-CSF, and EPO (FBS+S, 3, 6, GM, G, M, E). After 5 days of culture, the number of live cells was counted by flow cytometlic measurement of the frequency of propidium iodide negative cells related to the frequency of a known number of latex beads, as described in materials and methods. The bars show cell expansion as the mean number of live cells per input cell. The line crossing the bars indicates the relative input cell number as a reference point.

FIG. 3 depicts the frequency of granulocytic and monocytic cells among progeny from $CD34^{hi}$CD64+$CD71^{lo}$ cells after 5 days of culture in SF medium with or without M-CSF or medium supplemented with serum and SCF, IL-3, IL-6, GM-CSF, G-CSF, M-CSF and EPO (FBS+S, 3, 6, GM, G, M, E). Cultured cells originating from 10,000 sorted cells were stained with CD14 and CD15 and analyzed by flow cytometny as described in materials and methods. The dot plots show the expression of CD14 (x axis) and CD 15 (y axis) on live cells identified by combined measurement of light scatter and propidium iodide fluorescence. The histogram on top of each dot plot shows CD 14 fluorescence versus cell number the black histogram represents a constant number of latex beads included in the sample. The percentages represent the relative fraction of monocytic ($CD 14^{hi}$) and granulocytic ($CD 14^-$) progeny. The absolute numbers are given in paranthesis. The following abbreviations are used: N=neutrophilic granulocytes; B=basophilic granulocytes; M=monocytes/macrophages.

FIG. 4 depicts incorporation of BrdU in FBM $CD34^+$ cells incubated with and without SCF and M-CSF. Cells enriched for $CD34^+$ mrogenitors were starved for growth factors by incubation in SF medium for 24 h, and then incubated for additional 24 h in medium only (A) or with the addition of 40 ng/ml SCF (B) or 10 ng/ml M-CSF (C). For the last 6 h BrdU was added to the medium. The cells were then stained with CD34 APC, CD64 PE and anti-BrdU FITC, as described in materials and methods. The figure shows only $CD34^+$ cells. Dots above the dashed horizontal lines represent cells staining positively with CD64 relative to isotype control levels. Among these, gray dots represent $CD64^+$ cells that have not incorporated BrdU, whereas the black enlarged dots represent $CD64^+BrdU^+$ cells. The relative frequency of these two populations is shown as percentages.

FIG. 5 depicts the staining of FBM cells with the anti M-CSFR MoAb 3–4A4. Ammonium-chloride lysed FBM cells were labeled with anti M-CSFR (A,C,D,E) or rat IgG2b isotype control (B) and donkey-antirat RPE/BPE, followed by staining with CD34 FITC (A-E) and CD38 APC and CD50 perCP(C) or CD71 PerCP and CD64 APC (D,E). Panels A and B show unfractionated nucleated FBM cells. Panels C-E show staining of $CD34^+$ cells only, gated from the regions for both $CD34^{hi}$ and $CD34^{lo}$ cells, shown in Panel A. Primitive progenitor cells ($CD34^{hi}CD38^{lo}CD50^+$) are shown as enlarged black dots in panel C. Erythroid progenitor cells ($CD34^{lo}CD64^-CD71^{hi}$) are shown as enlarged black dots in panel D. Granulo-monocytic progenitor cells ($CD34^{hi}CD64^+CD71^{lo}$) are shown as enlarged black dots in panel E. The data are acquired on an experimental high sensitivity flow cytometer.

FIG. 6 depicts dot plots of ammonium-chloride lysed FBM cells which were enriched for $CD34^+$ cells and labeled with anti-M-CSFR (MoAb 3–4A4) and donkey-antirat RPE/BPE, followed by staining with CD34 FITC and CD64 APC. Panel B shows only CD34hi cells, which were gated on the region in panel A. The cells in panel B were further gated on a scatter region, corresponding to region 3 in FIG. 1B, These two regions were used as additional sort criteria to sort cells within each of the four regions in panel B. The two lower regions in panel B were set to include cells with staining comparable to isotype control levels.

FIG. 9 graphically depicts expression of CD34 on three different $CD34^{hi}$ subsets cultured for 60 h. $CD34^{hi}$ subsets were sorted according to differential expression of M-CSFR and CD64, as shown in FIG. 8A, cultured for 60 h and immunofluorescently labeled as described in the legend in FIG. 8. The level of CD34 on the cultured cells was then determined and is shown as histograms in the figure. The dashed line represents cells from the originally sorted $CD34^{hi}$ $M-CSFR^{hi}$ subset (upper region in FIG. 8A). The solid thin line represents cells from the originally sorted $CD34^{hi}CD64+M-CSFR^{lo}$ subset (lower right region in FIG. 8A) whereas the solid thick line corresponds to cells from the originally sorted $CD34^{hi}CD64-M-CSFR^{lo}$ subset (lower left region in FIG. 8A). The vertical line represents the lower border of the region used to soil $CD34^{hi}$ cells day 0.

DETAILED DESCRIPTION OF INVENTION

The present invention shows that the M-CSFR is expressed on 44±5% of $CD34^{hi}$ cells, which contain the majority of primitive progenitors and colony-foirning cells of the granulo-monocytic lineage. FACS™ sorting studies demonstrated that the M-CSFR positive population corresponded to the M-CSF-responsive cells and that these cells gave rise exclusively to granulo-monocytic colonies. $CD34^{hi}CD38^-$ cells were homogeneously negative and did not respond to M-CSF, suggesting that primitive progenitor cells are not targets for M-CSF. This suggests that effects of M-CSF reported earlier on primitive high proliferative potential (HPP) cells reflect effects on progeny that has differentiated during culture, or alternatively, that the M-CSF responsive HPP cells are more differentiated than the $CD34^{hi}CD38^{lo}CD50^+$ progenitors, and that functionally distinct subsets of granulo-monocytic progenitors can be isolated on the basis of differential surface expression of the M-CSFR and the granulo-monocytic marker CD64. Monocyte progenitors constituted approximately 70% of the CFCs among the $CD34^{hi}M-CSFR^{hi}$ cells, whereas 91% of the CFCs from the $CD34^{hi}CD64^+M-CSFR^{lo}$ population were CFU-G. Thus, the present study shows that M-CSFR is useful as a marker of granulo-monocytic lineage-commitment and to identify the divide between the pathways leading to granulocyte and monocyte differentiation.

Figure 1A:
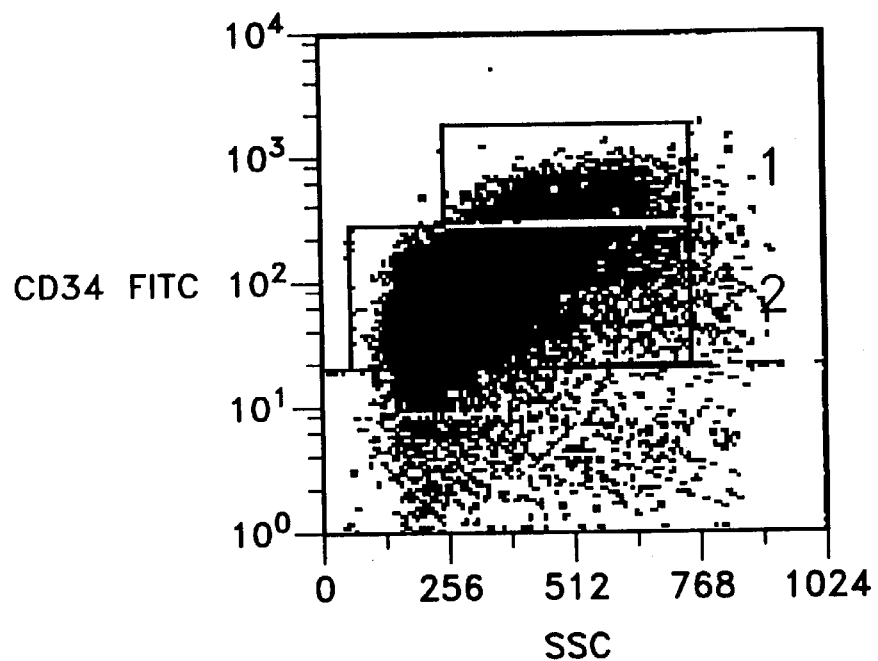
FIG. 1 presents dot plots for nucleated fetal bone marrow (FBM) cells enriched for CD34 cells by immunomagnetic separation were stained with CD34 FITC (A–D) in addition to CD38 APC and CD50 PE (C) or CD64 PE and CD71 biotin+ streptavidin-APC (D). Primitive progenitors were sorted as $CD34^{hi}$ $CD38^{lo}CD50^+$cells, i.e. those that simultaneously satisfy the criteria of regions 1, 3 and 5. Eiythroid progenitor cells were sorted as $CD34^{lo}$CD64–$CD71^{hi}$, i.e., those that simultaneously satisfy the criteria of regions 2, 3 and 6. FSC; forward light scatter, SSC; side scatter.
Figure 1B:
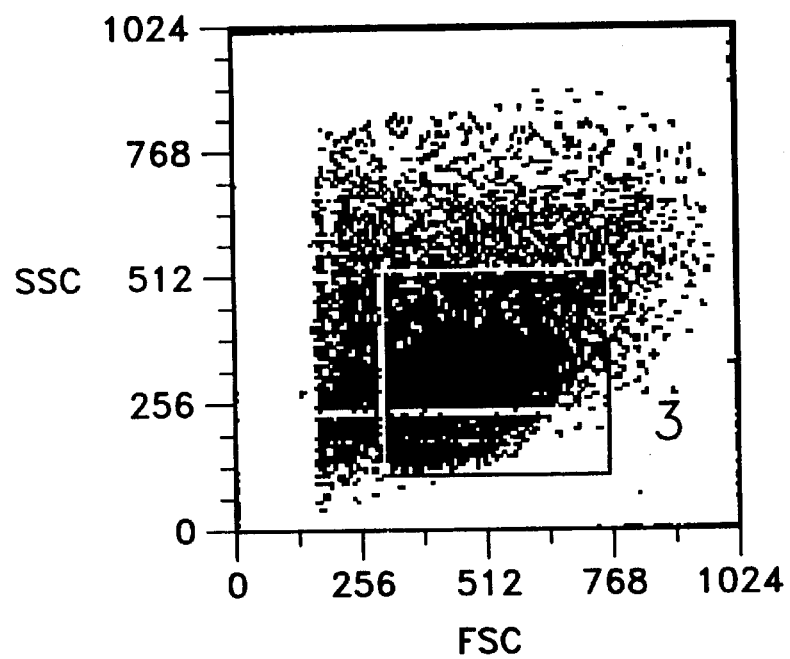
Figure 1C:
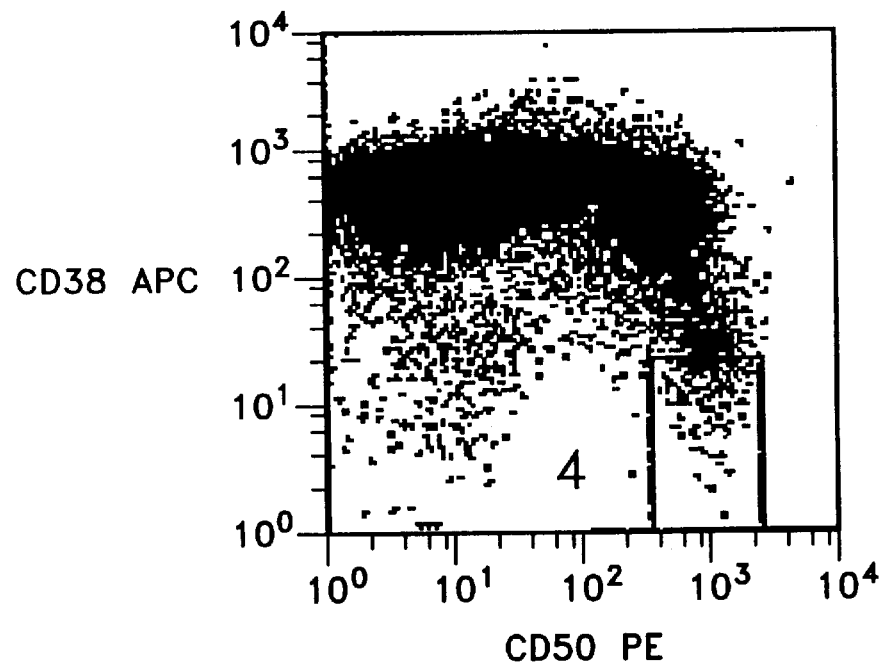
Figure 1D:
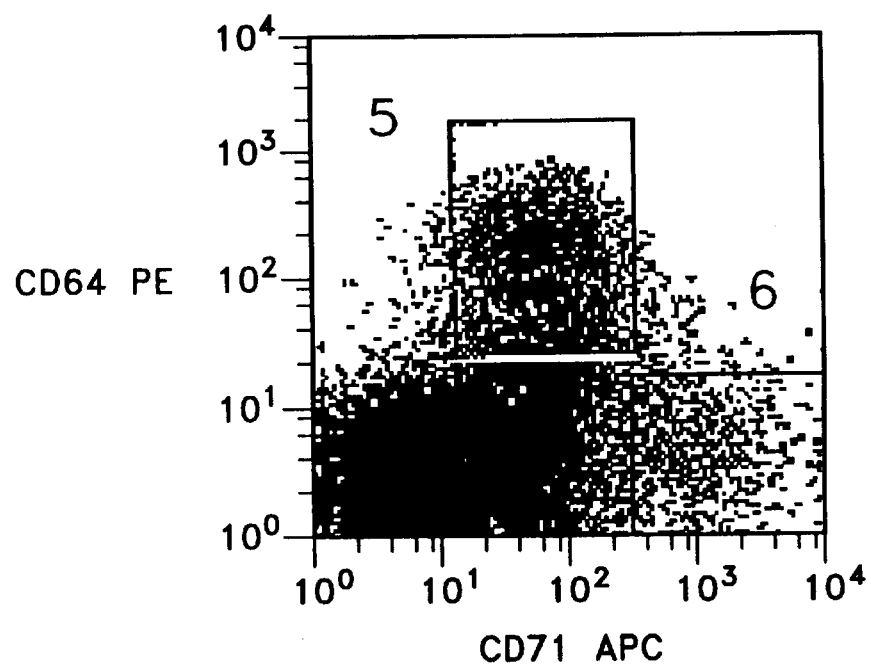
Figure 7:
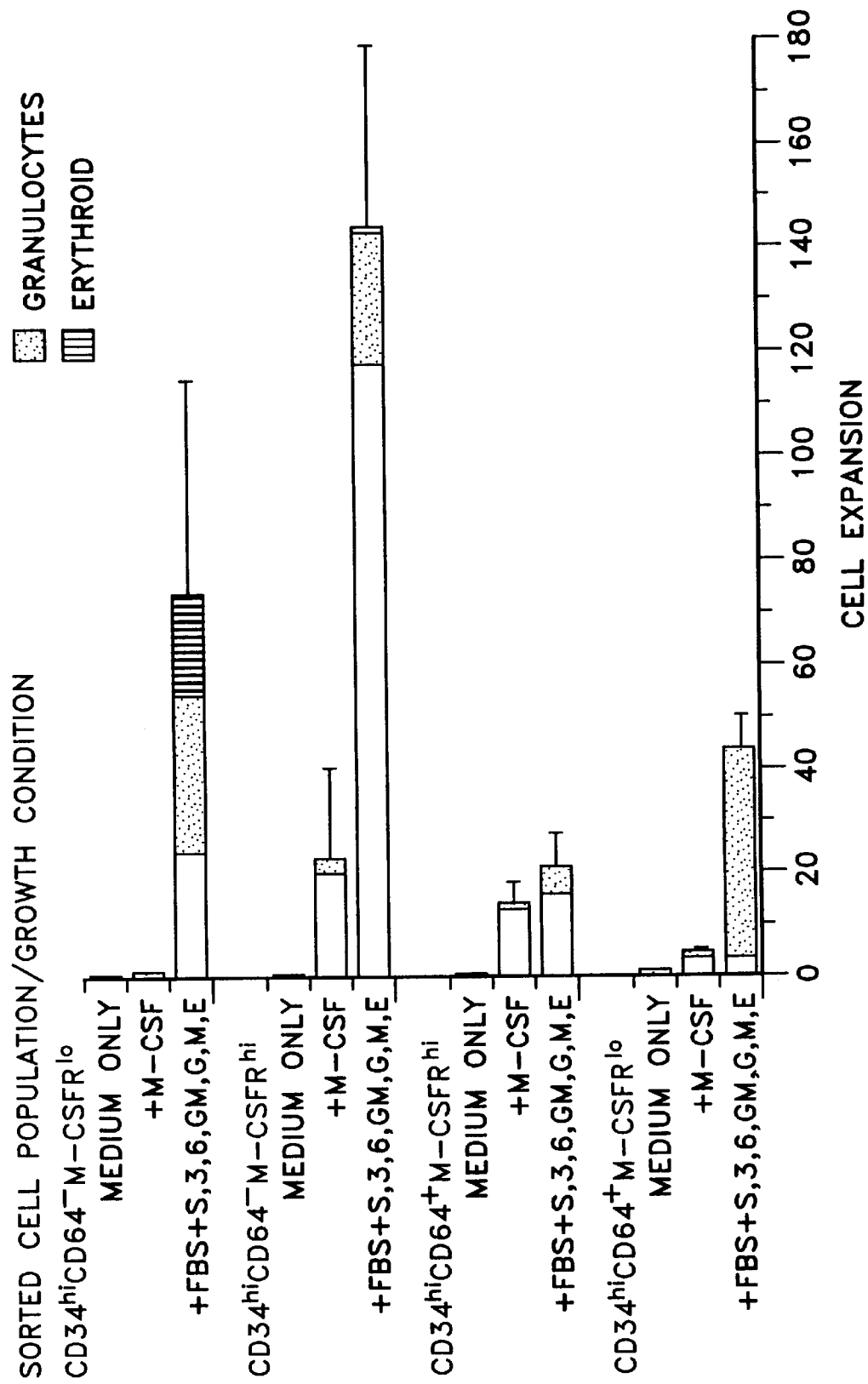
FIG. 7 graphically depicts the expansion of $CD34^{hi}$ subsets after 5 days of liquid culture. The indicated subsets were sorted as described in FIG. 6 and cultured in SF liquid medium without supplements (medium only) or with the addition of M-CSF or 20% fetal bovine serum and SCF, IL-3, IL-6 GM-CSF, M-CSF and EPO (FBS+S,3,6,GM,G,M,E), at concentrations as described in materials and methods. The cells were counted by flow cytometry using a constant number of latex beads as an internal standard. The progeny was classified as monocytic (white bars), granulocytic (black bars) or erythroid (striped bars) according to the staining pattern obtained with CD 14, CD15, CD48 and CD71, as described in materials and methods. The bars represent the average number of each cell type (viable cells) divided by the number of input cells for our experiments. Error bars indicate the total cell expansion for each sorted population.

CD64 was previously identified as the earliest specific marker for granulo-monocytic lineage commitment among a large number of candidate molecules. Several lines of evidence indicate, however, that M-CSFR appears before CD64 during the differentiation of most monocytic progenitors in the bone marrow. First, 31% of CFU-Ms were recovered from the $CD64^+M-CSFR^{hi}$ subset, whereas only 0.9% were found among the $CD64^+M-CSFR^{lo}$ cells. Second, the macrophage colonies formed by cells in the $CD64^-M-CSFR^{hi}$ population were larger and far more frequent than those derived from the two $CD64^+$ subsets. Third, whereas $CD64^+$ monocytic progenitors were expanded maximally by M-CSF alone, monocytic progenitors in the $CD64^-M-CSFR^{hi}$ subset could be expanded additionally in the presence of multiple cytokines (FIG. 7). Finally, cells in the $CD64^-M-CSFR^{hi}$ population expressed higher levels of CD34 than those that were $CD64^+$. The results in FIG. 8C show that a minor subset of $CD64^+M-CSFR^{lo}$ cells upregulated the M-CSFR in vitro and formed monocytes. Some of these cells could reflect contamination of the sort gates, as we have earlier shown that there may be a 2 to 6% contamination between erythroid and granulo-monocytic sort gates. On the other hand, studies of in vitro differentiation of primitive progenitors suggest that a substantial fraction of monocytic progenitor cells may regulate CD64 and M-CSF in the opposite order under certain conditions (FIG. 8D). M-CSFR and CD64 may therefore be regulated by the cells environment rather than as part of a fixed intrinsic differentiation program.

Whereas a recent study found that only 10% of murine CFU-Ms were M-CSFR positive, our results demonstrate that 55% of human CFU-M could be recovered from $M-CSFR^{hi}$ cells. This discrepancy may be species-related or due to differences in the methods used to detect the receptor. It was found that $CD34^+$ cells had to be incubated for several hours in serum-free medium before the receptor could be detected on the surface of most cells.

M-CSF and SCF both bind to tyrosine kinase type receptors. Studies on cell lines have suggested that M-CSF can use the SCFR signaling pathway to stimulate proliferation. From this it might be expected that SCF and M-CSF would induce similar proliferation in cells expressing both receptors. Our results demonstrated, however, that SCF expanded $CD34^{hi}CD64^+$ cells significantly less than M-CSF during five days of culture, although the levels of SCFR on these cells are comparable to or higher than those of M-CSFR. These data were further supported by the results showing that M-CSF induced a stronger mitotic response in CD34$^+$ CD64$^+$ cells than SCF during 24 h, as measured by BrdU incorporation. The results may therefore indicate that M-CSFR is coupled to signaling pathways that are qualitatively or quantitatively distinct from those activated via the SCFR in normal hematopoietic progenitor cells.

Cytokine target specificity can be mediated by at least two mechanisms; regulation of receptor expression and regulation of expression of molecules necessary to transmit signals from the receptor. We have recently shown that receptor distribution is sufficient to explain the specific effect of EPO on erythropoiesis, whereas SCF selectivity is determined in part by cell type-restricted expression of molecules other than the SCFR. In a previous study, forced expression of the M-CSFR into granulocytic progenitors failed to confer M-CSF responsiveness. This may indicate that M-CSF responsiveness depends on cell type-specific signaling molecules. The results from the present study suggest, however, that M-CSFR positive granulocytic progenitors can respond to M-CSF, as M-CSF alone leads to an increase in the number of granulocytic cells from the CD34$^{hi}$M-CSFR$^{hi}$ population after 5 days of culture. However, the effects of M-CSF on granulocyte development was found to be limited by rapid downmodulation of M-CSFR on granulocytic progenitors shortly after initiation of the culture, as demonstrated in FIG. 8. Lineage-dependent receptor regulation can also explain the small increase in the number of monocytic cells obtained after culture of the CD34$^{hi}$CD64$^+$M-CSFR$^{lo}$ population with M-CSF alone. Monocytic cells within this population up regulated the receptor during the 60 h culture period. The results showing that these cells were fully expanded in M-CSF alone (FIG. 7), suggest that they represent relatively late monocytic progenitors. This suggests that regulation of receptor expression is the predominant mechanism for M-CSF selectivity among human hematopoietic progenitor cells. Specificity for monocytic cells seems to be determined partly by induction of the receptor during or after commitment to the monocytic lineage and partly by downmodulation of the receptor during early granulocytic differentiation.

Figure 8:
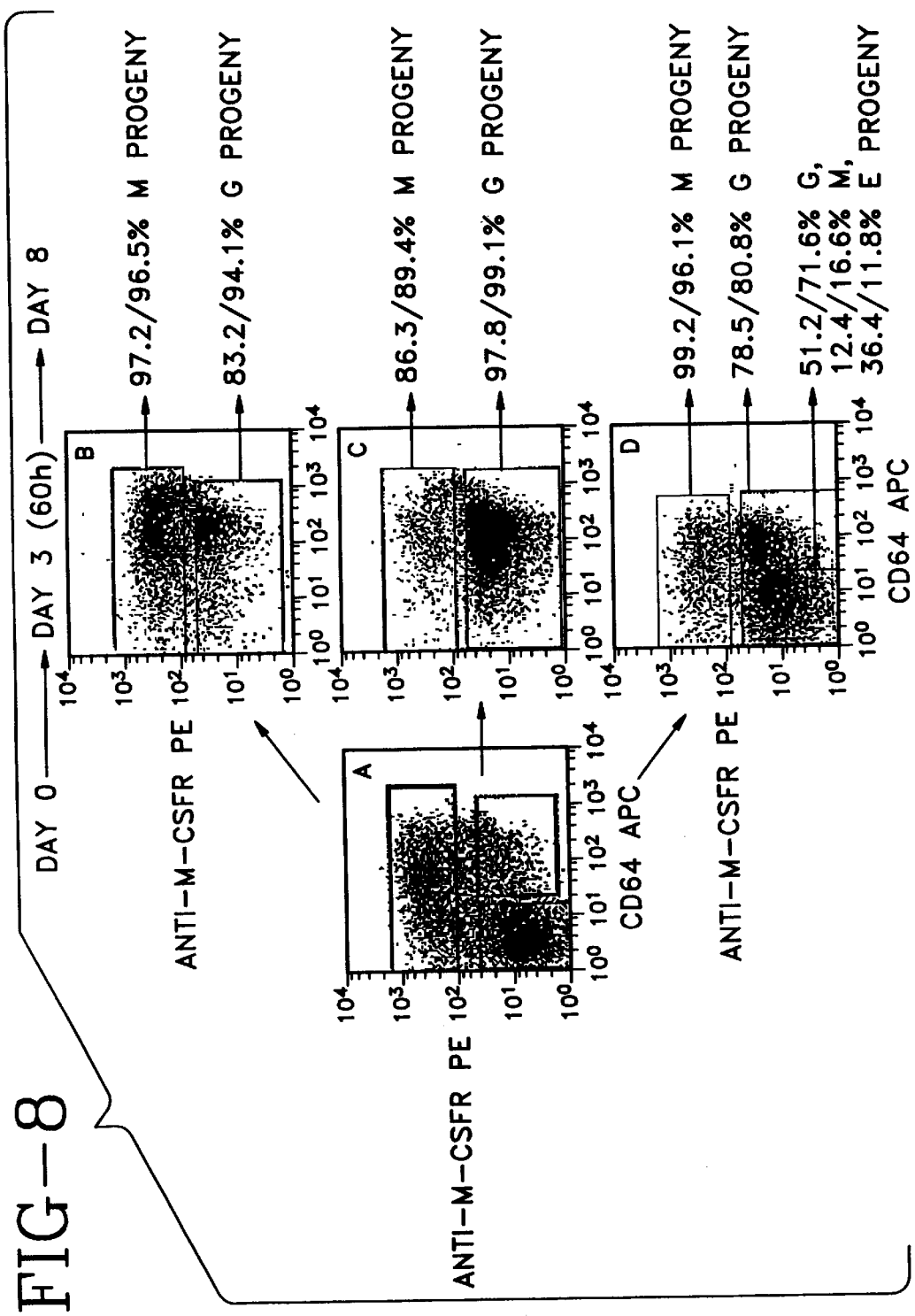
FIG. 8 depicts dot plots for CD34hi subsets at day 0 of culture and for the progeny of these cells when resorted after 60 h of culture. FBM cells enriched for $CD34^+$ cells were stained with anti-M-CSFR (MoAb 3–4A4) and donkey-antirat RPE/BPE, followed by staining with CD34 FITC and CD64 APC. Panel A shows $CD34^{hi}$ cells with the sort regions used. The three sorted populations were cultured in liquid SF medium supplemented with SCF, IL-3, IL-6, GM-CSF and G-CSF for 60 h and then stained again with anti-M-CSFR, donkey-antirat RPE/BPE, CD34 FITC and CD64. Following this, the cells were sorted according to the regions shown in panels B, C and D. The sorted cells were cultured in liquid medium supplemented with 20% FBS and SCF, IL-3, IL-6, GM-CSF, G-CSF and M-CSF for 5 additional days. The cultured cells were then stained with CD14, CD15, CD48, and CD71 and classified as monocytic (M), granulocytic (G) or erythroid (E) according to the staining pattern with these markers.

The results showing lineage-dependent regulation of CD64 and M-CSFR during early hematopoietic development are interesting in view of the detailed knowledge about the factors that regulate their expression. The promoters of M-CSFR and CD64 contain stimulatory binding sites for transcription factors of the ets family, including PU.1. There are also differences in their promoters that may explain the differences in regulation. The CD64 promoter contains an element that binds transcription factors of the STAT family including those induced by IL-6. Furthermore, the M-CSFR promoter has stimulatory binding sites for additional monocyte-specific factors as well as inhibitory binding sites for c-myb. Knockout experiments of PU.1 and c-myb have demonstrated essential roles for both factors in hematopoiesis, but it is not clear where in the differentiation process the molecules act. A recent study on embryonic stem (ES) cells from PU.1−/− mice demonstrated that PU.1 was necessary for differentiation-associated expression of CD64 and M-CSFR. However, in the ES system, these two molecules appeared at the stage of terminal differentiation, several days later than expression of CD14. It was therefore concluded that PU.1 primarily is important for late steps in monocytic development. In normal bone marrow, CD14 is a late monocytic marker that appears when the cells are CD34$^−$. The results from the present study showing that M-CSFR and CD64 are present on a substantial fraction of CD34$^{hi}$ cells, demonstrate that these are early myeloid markers and suggest that PU.1 may be involved at an early stage in hematopoietic development. The results also indicate that care should be taken before extending conclusions from ES cell differentiation systems to bone marrow progenitor cells. In FIG. 8, we present a system where small steps in myeloid differentiation can be studied by sorting homogeneous populations of progenitor cells at distinct stages in maturation and measuring differentiation-associated events during short term culture. When combined with sensitive methods for detection of gene regulation, such as the reverse transcriptase polymerase chain reaction (RT-PCR), this should be a powerful system to examine events associated with normal hematopoietic development. One question that may be immediately addressed is whether the levels of PU.1 are different in the populations, and if the expression of this factor changes when the cells differentiate in vitro. This type of experiment may also give the answer to why CD64 and M-CSFR seem to be regulated differently when primitive cells differentiate in vitro.

In conclusion, the present study shows that M-CSF target specificity among human hematopoietic progenitor cells is determined by lineage-specific regulation of the M—CSFR. The M-CSFR is a useful marker to isolate CFU-Gs and CFU-Ms and to study early granulo-monocytic differentiation in vitro.

EXAMPLES

The following examples illustrate certain preferred embodiments of the instant invention, but are not intended to be illustrative of all embodiments.

Example 1—Materials
Monoclonal Antibodies (MoAbs)

The anti-M-CSFR MoAb 3–4A4 (rat lgG2b) was provided by Dr. Richard Ashmun, St. Jude Children's Research Hospital, Memphis, Tenn., USA. This MoAb reacts specifically with the human M-CSFR, but does not block M-CSF ligand binding or biological activity. (The MoAb was clustered as CD115 during the Vth International Workshop on Leukocyte Differentiation Antigens.) MoAbs used to discriminate between non-committed and various lineage-committed progenitor cells included CD34 (HPCA-2), CD38 (Leu-17), CD19 (SJ25C1), CD71 (transferrin receptor), CD14 (Leu-M3), CD15 (Leu-M1) (all from Becton Dickinson and Company, San Jose, Calif.), CD50 (140–11, provided by Dr. Ramon Vilella, Servei d' lmmunologia, Hospital Clinic, Barcelona, Spain), CD48 (MEM102, from Dr. Vaclav Horejsi, Inst. of Molecular Genetics, Academy of Sciences of the Czech Republic, Prague) and CD64 (M22, MedaRex, Inc., Annandale, N.J., USA). The MoAbs were conjugated to fluorescein isothiocyanate (FITC), phycoerythrin (PE), peridinin chlorophyll protein (PerCP), allophycocyanin (APC), Cyanine 5 (Cy5) or biotin. Isotype control MoAbs included anti-keyhole limpet hemocyanin (mouse IgG1, BDIS), rat IgG2b (Phaimingen) and NC1 (mouse IgM) (Coulter Immunology, Hialeah, Fla., USA. Source: Vth International Workshop on Leukocyte Differentiation Antigens). MoAbs were titered to concentrations giving the highest specific staining. Most MoAbs to cytokine receptors were used at 10–20 μg/ml, adding 20 μl to 5×10$^5$ cells.

Secondary Reagents:

Polyclonal R-Phycoerythrin (RPE)-conjugated and B-Phycoerythrin (BPE)-conjugated F(ab')2 donkey-antirat- IgG heavy+light chain (mouse adsorbed) was from Jackson ImmunoResearch (West Grove, Pa., USA).

Cytokines and Media:

The serum-free medium consisted of Iscove's modified Dulbeccos medium with 25 mM Hepes buffer (Sigma Chemical Co., St. Louis, Mo., USA) supplemented with 200 µg/ml iron saturated transferrin (ICN Biomedicals, Inc., Costa Mesa, Calif., USA), 2% bovine serum albumine (Sigma), $5 \times 10^5$M 2-mercaptoethanol and penicillin and streptomycin at 100 µg/ml and 100 µg/ml, respectively (JRH Biosciences, Lenexa, Kans., USA). Just prior to use 50 µg/ml human low density lipoprotein (LDL) (Sigma) was added to this medium. For studies with serum-containing medium, 20% heat-inactivated fetal bovine serum (FBS) (Sigma) was added instead of LDL. Recombinant human interleukin-3 (rhIL-3), rhIL-6 and rh granulocyte-macrophage colony-stimulating factor (GM-CSF) were from Collaborative Biomedical Products. Rh stem cell factor (SCF) was from Peprotech (Rocky Hill, N.J., USA), rh macrophage colony-stimulating factor (M-CSF) from R&D Systems (Minneapolis, Minn., USA), rh erythropoietin (EPO) from CILAG AG (Schaffhausen, Switzerland) and rh granulocyte-CSF (G-CSF) from Amgen (Thousand Oaks, Calif., USA). Cytokines were added at final concentrations of 10 ng/ml rhGM-CSF, 10 ng/ml rhIL-3, 500 U/ml rhIL-6, 40 ng/ml rhSCF 50 ng/ml rhG-CSF, 10 ng/ml rhM-CSF and 2.5 U/ml rhEpo.

Cell Separation:

Human bone marrow from aborted fetuses of gestational age 17–22 weeks was obtained from Advanced Bioscience Resources (Alameda, Calif., USA) and The Anatomic Gift Foundation, Folkston, Ga., USA. The intramedullary cavities of upper and lower extremity bones were flushed with PBS-FCS, and the cell suspension centrifuged. The cell pellet was resuspended in PBS-FCS. Human adult bone marrow from healthy donors was provided by Dr. Ping Law, Stem Cell Laboratories, Division of Hematology and Oncology, University of California San Diego, USA. Adult bone marrow and cell suspensions from fetal bone marrow (FBM) was diluted ten-fold in a solution containing 0.9% $NH_4Cl$, 0.1% $KHCO_3$ and 0.0037% tetrasodium EDTA in double-distilled $H_2O$ (pH 7.2, 20° C.) to lyse mature red blood cells. After 5 min. of lysing, cells were centrifuged, washed twice in PBS-FCS and filtered through a 70 µm nylon filter (Becton Dickinson and Company, Franklin Lakes, N.J., USA) for subsequent staining.

Cell Staining:

To minimize non-specific antibody binding, cells were preincubated with PBS containing 0.5% human gamma globulin (Sigma). For indirect immunofluorescence staining, nucleated bone marrow cells were incubated with an unlabeled MoAb, washed twice in PBS-FCS and stained with fluorochrome-conjugated secondary antibodies. All incubation steps were performed on ice for 25 min. Immunostained cells were either kept on ice and analyzed immediately by flow cytometry or fixed in 0.5% paraformaldehyde and analyzed within 24 hours.

Flow Cytometric Analysis:

Immunostained cells were analyzed using an experimental high-sensitivity flow cytometer. This flow cytometer is equipped with three lasers; a 488-nM Argon Ion laser (15 mW) for excitation of PerCP and FITC, a 633-nm Helium-Neon laser (10 mW) for excitation of APC or Cy5 and a 532-nm YAG laser (20 mW) for excitation of PE. The 532-nm excitation of PE yields six times the signal-to-noise ratio obtained with 488-nm excitation. For each sample 10,000–50,000 events were acquired in list mode with CELL Quest™ software (Becton Dickinson and Company).

Forward light scatter, orthogonal light scatter and four fluorescence signals were determined for each cell, and the listmode data files were analyzed on a Macintosh computer with Paint-A-Gate$^{PRO}$™ (Becton Dickinson and Company). The instrument was calibrated using fluorescent particles to allow direct comparison between staining intensities measured in different experiments. Dead cells were identified by positive staining with propidium iodide (PI) (Molecular Probes Inc., Eugene, Oreg.) at a final concentration of 1 µg/ml.

Immunomagnetic Purification of CD34±Cells:

Before cell sorting, $CD34^+$ cells were purified from nucleated bone marrow cells using a separation kit from Miltenyi Biotech (Auburn, Calif., USA) according to the description from the manufacturer. The purification method routinely gave $CD34^+$ cells that were more than 90% pure and the yield was typically 70–80% (results not shown). Purified cells were then stained with CD34 FITC (HPCA-2, BDIS) and fluorochrome- or biotin-conjugated MoAbs to other antigens to allow flow cytometric sorting of progenitor cell subsets.

Example 2

Measurement of Bromodeoxyuridine (BrdU) Incorporation:

Immunomagnetically purified $CD34^+$ cells were cultured for 24 h in serum free (SF) medium only, followed by 24 h culture with or without the addition of 40 ng/ml SCF or 10 ng/ml M-CSF. BrdU (Sigma) was added to the culture for the last 6 h at a final concentration of 60 µM. After the culture period the cells were washed twice in PBS—FCS, stained with CD34 APC and CD64 PE and fixed in 0.5% paraformaldehyde (100 µl/sample) at 4° C. After 4 h 22 µl PBS containing 5% Tween 20 (Sigma) was added and the cells were incubated for 12 additional hours at 4° C. The cells were then washed twice in PBS. Twenty microliters of PBS containing 10 mg/ml DNAse I (Sigma Cat no. DN-25)) and 4 µg/ml anti-BrdU FITC MoAb (BDIS) was added to the cell pellets. The cells were incubated for a minimum of 1 h at room temperature followed by the addition of 200 µl PBS before the samples were analyzed on the flow cytometer.

Example 3

Cell Sorting and Culture:

Inununostained cells were sorted by a FACS VANTAGE™ flow cytometer equipped with an Automated Cell Deposition Unit. FITC and PE fluorescence was excited by a 488-nm Argon Ion laser and APC or Cy5 fluorescence by a 90 mW Spectrum laser tuned at 647 nm. To eliminate doublets and cell aggregates, a pulse processor module was used on the forward light scatter parameter. The gates defining cells staining positively with MoAbs were set to include less than 2% of cells stained with isotype control. For determination of colony-forming potential, cells were sorted singly into 96-well plates (Falcon Labware) containing serum supplemented medium and the concentrations of SCF, IL-3, IL-6, GM-CSF, G-CSF, M-CSF and EPO described above. For determination of cytokine effects on populations, each cell subset was sorted into polypropylene tubes containing the serum free (SF) medium described above. The cells were then equally distributed between individual wells in a 24-well plate (Falcon Labware) and serum and cytokines were added as indicated at the concentrations described above.

Example 4

Determination of Colony Size and Type:

96-well plates containing singly sorted cells were examined for the presence of progeny after 14 days of culture by examination through an inverted light microscope. The colonies were initially classified in four categories according to size. Type I colony: 40–100 cells. For colony types II–IV, colony sizes were compared to cell numbers by counting cells from individual colonies by flow cytometry using a fixed number of fluorescent latex beads as standards, as described earlier. Type II colony: more than 100 cells, but covering less than 25% of the area of the well (average cell number=1871, range 102–10 595, n=48). Type III colony: covering 25–50% of the area of the well (average cell number=41 924, range 5162–84 483, n=32). Type IV colony: covering more than 50% of the area in the well (average cell number=316 640, range 80 593–823 034, n=26). The cellular content of individual colonies was determined by staining each colony with CD14 FITC, CD15 PE, CD71 PerCP and CD48 APC and the non-vital DNA dye propidium iodide (PI), followed by four-color flow cytometric analysis. CD14 is expressed on monocytic cells and CD15 is upregulated during myeloid differentiation and is primarily expressed on granulocytic cells. CD71 is highly expressed, although not specific for, erythroid cells, and CD48 a leukocyte specific marker. The combination of these four markers allows the specific identification of granulocytic, monocytic and erythroid cell subsets. Granulocytic and monocytic cells were both classified as $CD48^+$ and $CD71^{lo}$. Neutrophilic granulocytes were further identified as $CD14^-CD15^{hi}$, basophilic granulocytes as $CD14^-CD15^{medium}$, whereas monocytic cells were classified as $CD14^{hi}CD15^{lo}$ (see FIG. 3). Erythroid cells were characterized as $CD14^-CD15^{lo}CD48^{lo}CD71^{hi}$. Colonies containing less than 300 cells were pooled according to their growth pattern as macrophages, granulocytic cells or erythroid cells and analyzed by flow cytometry. The flow cytometric classification was validated by Wright Giemsa staining of selected colonies.

Example 5
M-CSF Induces Expansion of Granulo-Monocytic but not Primitive and Erythroid Progenitors During Five Days of Culture.

$CD34^+$ subsets previously shown to be highly enriched for primitive, erythroid and granulo-monocytic progenitors were sorted and cultured to determine whether M-CSF acted differently on the cell types. The population identified as $CD34^{hi}$ in the present study was set to include on average 15.7±1.5% of the $CD34^+$ cells (n=4). Primitive hematopoietic progenitors were defined as $CD34^{hi}CD38^{lo}CD50^+$ (regions 1, 3 and 4 in FIG. 1). CD50 was used to discriminate hematopoietic cells from $CD34^{hi}CD38^{lo}$ stromal progenitor cells. CD64 is specifically expressed by cells committed to the granulo-monocytic lineage, and granulo-monocytic progenitors were defined as $CD34^{hi}CD64^+CD71^{lo}$ (regions 1, 3 and 5 in FIG. 1). Erythroid progenitors were defined as $CD34^{lo}CD64^-CD71^{hi}$ (regions 2, 3 and 6 in FIG. 1). Cells were harvested after 5 days of culture, counted and stained with CD14, CD 15, CD48, and CD71, which allows discrimination between differentiated neutrophilic granulocytes, basophilic granulocytes, monocytic and erythroid cells, as described in materials and methods. Addition of M-CSF to the medium did not increase the number of viable progeny from primitive progenitors ($CD34^{hi}CD38^{lo}CD50^+$) or erythroid progenitors ($CD34^{lo}CD64^-CD71^{hi}$)(FIG. 2). This was not due to lack of factors necessary for promoting cell survival, as M-CSF did not increase proliferation significantly in the presence of SCF (FIG. 2). Both progenitor types proliferated extensively when cultured in medium containing serum and SCF, IL-3, IL-6, GM-CSF, G-CSF, M-CSF and Epo (hereafter denominated FBS+S,3,6,GM,G,M,E), demonstrating that the cells were not damaged by the cell sorting (FIG. 2). Granulo-monocytic progenitors ($CD34^{hi}CD64^+CD71^{lo}$) proliferated extensively (19.5±2.9 fold, n=4) in the presence of M-CSF. M-CSF induced 5.5 fold higher expansion of the $CD34^{hi}CD64^+$ cells than SCF (p=0.0001, n=4), and the two factors did not act synergistically to induce proliferation of this subset.

$CD34^+CD64^+$ cells give rise to neutrophilic granulocytes, basophilic granulocytes and monocytes after 5–7 days of culture. These populations can be discriminated as distinct subsets by combined measurement of CD14 and CD15 (FIG. 3). Cells cultured in the presence of FBS+S,3,6,GM,G,M,E gave rise to 42±7.5% granulocytic cells and 58±3.1% monocytic cells (n=4) (FIG. 3). In contrast, 91±2.8% (n=4) of the cells formed in the presence of M-CSF alone were monocytic (FIG. 3). M-CSF alone induced on average 45% of the expansion monocytic cells observed in the "optimized" medium, but on average only 6% of the expansion of granulocytic cells. These results suggest that M-CSF acts specifically on progenitors committed to the granulo-monocytic lineage and predominantly promotes the outgrowth of monocytes from these cells.

Example 6
M-CSF is a Stronger Mitotic Stimulus for Granulo-Monocytic Progenitor Cells than SCF.

M-CSF induced a significantly higher expansion than SCF of the granulo-monocytic $CD34^{hi}CD64^+$ cells during five days in culture (FIG. 2). To exclude that this was due to differentiation-associated regulation of the receptors, we measured the proliferation induced by M-CSF and SCF directly in $CD34^+CD64^+$ cells after 24 h in culture with M-CSF or SCF. Cells enriched for $CD34^+$ progenitors were starved for growth factors by incubation in serum-free medium for 24 h, and then incubated for additional 24 h in medium only (FIG. 4A) or with the addition of 40 ng/ml SCF (FIG. 4B) or 10 ng/ml M-CSF (FIG. 4C). For the last 6 h BrdU was added to the medium. The cells were then stained with CD34, CD64 and anti-BrdU as described in materials and methods. The results showed that M-CSF induced a 3 to 3.2 fold (n=2) increase in the number of $CD34^+CD64^+$ cells incorporating BrdU relative to medium alone, whereas SCF only induced a 1.4 to 1.7 fold increase (n=2). No anti-BrdU-positive cells were detected in controls that were incubated without BrdU. No significant expansion for the total cell population could be detected after the 24 h incubation with cytokines. These data indicate that the stronger mitotic stimulus induced by M-CSF as compared with SCF in granulo-monocytic progenitor cells, is a direct effect.

Example 7
M-CSFR is Expressed on Granulo-Monocytic Progenitors but not on Primitive, Erythroid and Lymphoid Progenitors.

M-CSFR expression was correlated to the esponsiveness of cells to M-CSF by staining cells with MoAbs to the M-CSFR (3–4A4), CD34 and the markers used for cell sorting shown in FIG. 1. Anti-M-CSFR MoAbs stained freshly isolated $CD34^+$ cells weakly (not shown). However, after overnight incubation of the cells in SF medium, on average 44±5% (n=3) of the CD34$^{hi}$ cells were positive for the M-CSFR (FIG. 5A). The populations enriched for primitive (CD34$^{hi}$CD38$^{lo}$CD50$^+$) and erythroid progenitor cells (CD34$^+$CD64$^-$CD71$^{hi}$) are shown as enlarged black dots in FIG. 5C and D, respectively. These cells did not stain more brightly with anti-M-CSFR than with isotype control MoAbs. Granulo-monocytic progenitors (CD34$^{hi}$CD64$^+$CD71$^{lo}$) stained heterogeneously with anti-M-CSFR MoAbs (FIG. 5E). In addition, a subset of CD34$^+$CD64$^-$M-CSFR$^+$ cells was observed (FIG. 5E). These cells had higher expression of CD34 than the CD64$^+$ cells, suggesting that they may represent early progenitor cells. B-lymphoid progenitors (CD34$^+$CD19$^+$) did not stain more with anti-M-CSFR than with isotype controls. The staining of adult bone marrow CD34$^+$ cells was highly similar to that observed for fetal bone marrow cells (not shown, n=3). Incubation of bone marrow cells with M-CSF resulted in a 70% reduction in staining with the anti-M-CSFR MoAb.

Example 8
M-CSFR Expression Correlates to M-CSF Responsiveness

CD34$^{hi}$ cells are enriched in clonogenic progenitor cells and CD64 represents the earliest granulo-monocytic marker described for this subset. We next investigated whether CD34$^{hi}$ cells with different levels of CD64 and M-CSFR contained different types of granulo-monocytic progenitors. The CD34$^{hi}$ cells (within the region in FIG. 6A) were sorted as four populations according to the regions in FIG. 6B. These were CD64−M-CSFR$^{lo}$ (48.9±4.8%, n=4), CD64$^-$M-CSFR$^{hi}$ (14.0±13.1%, n=4), CD64$^+$M-CSFR$^{hi}$ (20.1±1.6% n=4) and CD64$^+$M-CSFR$^{lo}$ (7.1±2.6% n=4) (FIG. 6B). To simplify the interpretation of the data, sort regions were set apart to exclude cells with low to intermediate M-CSFR levels (9.9±3.4% of CD34$^{hi}$ cells). The cells that expressed M—CSFR but not CD64 (upper left region in FIG. 6B) had 21±4% and 33±9% higher levels of CD34 than the CD64$^+$M-CSFR$^{hi}$ (upper right region) and CD64$^+$M-CSFR$^{lo}$ subsets (lower right region), respectively (p<0.006, n=4). The M-CSFR$^{hi}$ cells lacking CD64 may therefore represent earlier progenitor cells than those expressing CD64. After 5 days in culture, the progeny were counted and the cellular content determined by staining with CD14, CD15, CD48 and CD71, as described in materials and methods. M-CSF responsiveness correlated well with receptor expression, although M-CSF induced a small increase in the number of monocytes obtained from CD64$^+$M-CSFR$^{lo}$ cells (FIG. 7). There was furthermore a clear difference in the relative number of monocytes and granulocytes obtained after culture of the subsets with FBS+S,3,6,GM,G,M,E. The population that was negative both for CD64 and M-CSFR gave rise to similar amounts of monocytes and granulocytes and also to erythroid cells (FIG. 7). The three other populations gave rise exclusively to granulo-monocytic progeny. The majority of cells obtained from the two M-CSFR$^{hi}$ populations was monocytic (75±3% and 83±6%, respectively, n=3), whereas 91±3% of the cells from the CD64$^+$M-CSFR$^{lo}$ population were granulocytes (n=3). These results demonstrate that M-CSFR expression is different on granulocytic and monocytic progenitor cells.

Among the M-CSFR$^{hi}$ cells there was a clear difference in the expansion potential of the subsets that were positive or negative for CD64. The two populations showed a similar expansion in the presence of M-CSF alone. However, addition of serum and multiple cytokines led to a six-fold increase in the expansion of the CD64$^-$M—CSFR$^{hi}$ cells (p=0.003, n=3), but to no significant increase in the expansion of the CD64$^+$M-CSFR$^{hi}$ cells. Likewise, monocytic cells derived from the CD64$^+$M-CSFR$^{lo}$ population were maximally expanded by M-CSF alone (FIG. 7). These results further suggest that CD64$^+$ monocytic progenitors are more differentiated than those in the CD64$^-$M-CSFR$^{hi}$ population.

Example 9
CD34$^{hi}$ Subsets Defined by Differential Expression of CD64 and M-CSFR Contain Distinct Types of Colony-Forming Cells.

The colony forming potential of the four CD34$^{hi}$ populations in FIG. 6B was examined by single cell sorting and phenotypic analysis of day 14 progeny as described in materials and methods. The CD34$^{hi}$CD64$^-$M-CSFR$^{lo}$ population (FIG. 6B) was the only subset containing cells forming mixed and erythroid colonies. This subset also gave rise to the highest fraction of large colonies, as 61±7% of the colonies covered 25% or more of the well (i.e. type III and IV colonies, see materials and methods). The three subsets expressing either M-CSFR or CD64 or both formed exclusively granulo-monocytic colonies (Table I). Both of the M-CSFR$^{hi}$ subsets formed colonies of which more than 80% contained monocytic cells and approximately 70% were CFU-M (n=3). The highest cloning frequency and frequency of bipotent colonies was observed for the CD64- fraction. Furthermore, of the colonies formed by the CD64$^-$M-CSFR$^{hi}$ cells 18±9% covered more than 25% of the well, whereas only 7±5% of the colonies from the CD64+M-CSFR$^{hi}$ were of this size. The CD64$^+$M-CSFR$^{lo}$ subset consisted almost entirely of granulocytic progenitors (90.9±3.1% n=3), and 36±11% of these colonies covered more than 25% of the well. These results demonstrate that CFU-Ms and CFU-Gs can be discriminated by combined measurement of CD34, CD64 and the M-CSFR.

TABLE 1

| Sorted Cell Subset | % CFU-G | % CFU-M | % CFU-GM | %CFU-G/M/GM | % BFU-E/CFU-E | % CFU-MIX | Cloning Frequency |
|---|---|---|---|---|---|---|---|
| CD34$^{hi}$CD64$^-$M-CSFR$^{lo}$ | 12.6 ± 6.8 | 34.8 ± 9.6 | 30.7 ± 10 | 78.1 ± 6.9 | 8.5 ± 3.4 | 13.4 ± 3.3 | 34.0 ± 1.8 |
| CD34$^{hi}$CD64$^-$MCSFR$^{hi}$ | 13.7 ± 6.8 | 67.4 ± 11.9 | 18.9 ± 5.8 | 100 ± 0.0 | 0.00 | 0.00 | 50.2 ± 3.1 |
| CD34$^{hi}$CD64$^+$M-CSFR$^{hi}$ | 17.1 ± 7.8 | 7.1 ± 5.3 | 11.8 ± 2.5 | 100 ± 0.0 | 0.00 | 0.00 | 26.2 ± 5.8 |
| CD34$^{hi}$CD64$^+$M-CSFR$^{lo}$ | 90.0 ± 3.1 | 4.3 ± 4.6 | 4.5 ± 2.3 | 99.7 ± 0.6 | 0.3 ± 0.6 | 0.00 | 45.7 ± 6.3 |
| CD34$^{hi}$ | 22.1 ± 5.3 | 42.6 ± 5.4 | 22.6 ± 6.1 | 87.3 ± 4.6 | 5.0 ± 1.8 | 7.7 ± 2.6 | 36.1 ± 4.2 |

Interestingly, almost all the CFU-Ms and CFU-GMs from the CD34$^+$ cells could be recovered from the CD34$^{hi}$ cells (Table II). In contrast, only 51% of the CFU-Gs were derived from the CD34$^{hi}$ fraction (Table II). Nearly all the remaining CFU-Gs, as well as all the remaining CFU-Ms and CFU-GMs, were recovered from the CD34$^{lo}$CD64$^+$ fraction (not shown). The percentage of granulo-monocytic colonies from CD34$^+$ cells that could be recovered from cells expressing CD64 or M-CSFR or both was calculated by comparing the frequencies of colony forming cells in these populations to that of the whole CD34$^+$ population. In three experiments, 64.9±4.5% of the granulo-monocytic colonies were recovered from the purely granulo-monocytic CD34$^+$CD64$^+$ and/or M-CSFR$^+$ fractions.

TABLE II

| Sorted Cell Subset | % CFU-G | % CFU-M | % CFU-GM |
|---|---|---|---|
| CD34$^{hi}$CD64$^-$M-CSFR$^{lo}$ | 13.9 ± 8.4 | 38.0 ± 9.4 | 61.6 ± 22.2 |
| CD34$^{hi}$CD64$^-$M-CSFR$^{hi}$ | 6.4 ± 2.9 | 31.1 ± 7.0 | 16.1 ± 4.1 |
| CD34$^{hi}$CD64$^+$M-CSFR$^{hi}$ | 6.0 ± 3.8 | 24.3 ± 4.0 | 7.5 ± 1.0 |
| CD34$^{hi}$CD64$^+$M-CSFR$^{lo}$ | 19.6 ± 3.4 | 0.9 ± 0.8 | 1.8 ± 0.9 |
| CD34$^{hi}$ | 51.3 ± 6.7 | 97.4 ± 3.1 | 95.2± 2.5 |

Example 10
Granulocytic Differentiation of CD34$^{hi}$ M-CSFR$^{hi}$ cells is Associated with Rapid Downmodulation of the M-CSFR.

The presence of granulocytic progenitors within the CD34$^{hi}$M-CSFR$^{hi}$ populations suggested that the relationship between M-CSFR expression and monocyte lineage-commitmnent is not absolute during early hematopoietic differentiation. We therefore investigated the possibility that the receptor may be regulated in a lineage-dependent way during the subsequent stages of differentiation. Sorted CD34$^{hi}$M-CSFR$^{hi}$ cells (FIG. 8A, upper region) were stained with MoAbs to CD34, CD64 and M-CSFR after 60 h of culture in SF medium containing SCF, IL-3, IL-6, GM-CSF and G-CSF. As shown in FIG. 8B the large majority of the cells expressed relatively high levels of CD64 after the culture. In addition, distinct subsets of M-CSFR$^{hi}$ (62–71%, n=2) and M—CSFR$^{lo}$ cells (38–29%, n=2) could be discriminated. These subsets were sorted and cultured for additional 5 days. Combined staining of the progeny with CD14 and CD15 demonstrated that the M-CSFR$^{hi}$ subset (FIG. 8B, upper region) had developed into a homogeneous population of monocytic cells, whereas the M-CSFR$^{lo}$ subset (FIG. 8B, lower region) generated almost purely granulocytic progeny. The number of viable cells obtained after secondary culture of M-CSFR$^{hi}$ cells was 53–210 fold (n=2) higher in the presence of M-CSF than with medium only (p=0.04), and the addition of FBS+S,3,6,GM,G,M,E did on average not increase the number of cells further. In contrast, M-CSF had no effect on M-CSFR$^{lo}$ cells, whereas these cells expanded 23–78 fold (n=2) in the presence of FBS+S,3,6,GM,G,M,E (p=0.03). This demonstrates a close correlation between receptor expression and cytokine responsiveness. The results show that granulocytic development of CD34$^{hi}$M-CSFR$^{hi}$ cells is associated with a dowmnodulation of the M-CSFR and that M-CSFR$^{hi}$ cells are precursors for CD64+M-CSFR$^{lo}$ cells.

Example 11
A Minor Fraction of CD34$^{hi}$CD64±M-CSFR$^{lo}$ Upregulate the M-CSFR and Develop into Monocytes As shown in FIG. 7 and Table I, the CD34$^{hi}$CD64$^+$M-CSFR$^{lo}$ population contained minor fractions of M-CSF responsive monocytic cells. We therefore examined whether subsets of cells in this population (FIG. 8A, lower right region) upregulated the M-CSFR during culture. Sorted CD34$^{hi}$CD64$^+$M-CSFR$^{lo}$ cells were cultured for 60 h and stained with CD34, CD64 and anti-M-CSFR. FIG. 8C shows that a small subset of M-CSFR$^{hi}$ cells (4–8%, n=2) was observed. These cells gave rise to almost exclusively monocytic progeny, whereas the cells that remained M-CSFR$^{lo}$ gave rise to granulocytes. The data correspond well with the results showing that 9% of the clonogenic CD64$^+$M-CSFR$^{lo}$ cells generated monocytic progenitor cells (Table I) and suggest that monocytic differentiation of these cells is associated with rapid upmodulation of the M-CSFR.

Example 12
The Majority of Primitive Progenitors Upregulate CD64 before the M-CSFR when Cultured in Vitro The data in FIG. 8 A–C demonstrate that the M-CSFR can be used to follow monocytic and granulocytic differentiation in vitro. To determine whether the M-CSFR could be used to monitor commitment of more primitive cells to the granulo-monocytic lineage, CD34$^{hi}$ cells that were negative for both markers (FIG. 8A, lower left region) were sorted and cultured. However, the staining pattern of CD64 and M-CSFR shown for freshly isolated cells in FIG. 8A was not reproduced when primitive cells differentiated in vitro. As many as 21–36% of CD34$^{hi}$CD64$^-$M-CSFR$^{lo}$ cells had upregulated CD64 after 60 h (lower right region) but only 7–16% were M-CSFR$^{hi}$ (upper region). Nearly all the cells that upregulated the receptor gave rise to monocytic progeny, whereas 80% of the cells generated from the CD64$^+$M-CSFR$^{lo}$ subset were granulocytic. These results may suggest that the upregulation of M-CSFR early in granulo-monocytic differentiation depends on factors that are present in the normal hematopoietic environment, but absent under the culture conditions used here. By day 3 the majority of the cells remained CD64$^-$M-CSFR$^{lo}$ (lower left region, FIG. 8D) and gave rise to a mixture of granulocytic, monocytic and erythroid cells in secondary culture.

Example 13
Regulation of CD34 During differentiation of CD34$^{hi}$Subsets in vitro After 60 h of culture the cells originating from the CD34$^{hi}$M-CSFR$^{hi}$ and CD34$^{hi}$CD64$^+$M-CSFR$^{lo}$ populations shown in FIG. 8A were still CD34$^+$ (dashed and solid thin lines, respectively, in FIG. 9). However, these cells expressed homogeneously lower levels of CD34 than at day 0 of culture, represented by the vertical line in FIG. 9. In contrast, the cells originating from the CD34$^{hi}$CD64$^-$M-CSFR$^{lo}$ population in FIG. 8A (solid thick line in FIG. 9) showed heterogeneous levels of CD34, with a subset remaining CD34$^{hi}$ at 60 h of culture (to the right of the vertical line in FIG. 9). Furthermore, most of the progeny from the CD34$^{hi}$CD64$^-$M-CSFR$^{lo}$ cells had higher CD34 levels than the cells expressing CD64 and/or M-CSFR. These results indicate a clear distinction between CD34$^{hi}$ cells with different expression of M-CSFR and CD64, and suggest that the cells in the sort regions in FIG. 8A represent populations of progenitor cells at distinct stages of differentiation.

It is apparent that many modifications and variations this invention as hereinabove set forth may be made without departing from the spirit and scope thereof The specific embodiments are given by way of example only and the invention is limited only by the terms of the appended claims.

What is claimed is:
1. A method of distinguishing progenitors committed to the granulo-monocytic lineage in a population containing CD34$^+$ cells, comprising: contacting said cells with antibod- ies specific for CD34, M-CSFR and CD64; and then flow cytometrically detecting cells that are CD34$^{hi}$M-CSFR$^+$CD64$^-$ wherein a CD34$^{hi}$ M-CSFR$^+$CD64$^-$ phenotype indicates granulo-monocytic lineage progenitor cells.

2. A method of isolating progenitors committed to the granulo-monocytic lineage from a population containing CD34$^+$ cells, comprising: contacting said cells with antibodies specific for CD34, M-CSFR and CD64; and then flow cytometrically isolating cells that are CD34$^{hi}$M-CSFR$^+$CD64$^-$ wherein a CD34$^{hi}$M-CSFR$^+$CD64$^-$ phenotype indicates granulo-monocytic lineage progenitor cells.

3. A method of enriching a population containing CD34$^+$ cells for progenitors committed to the granulo-monocytic lineage, comprising: contacting said cells with antibodies specific for CD34, M-CSFR and CD64; and then flow cytometrically enriching cells that are CD34$^{hi}$M-CSFR$^+$CD64$^-$ wherein a CD34$^{hi}$M-CSFR$^+$CD64$^-$ phenotype indicates granulo-monocytic lineage progenitor cells.

4. A method of depleting a population containing CD34$^+$ cells of progenitors committed to the granulo-monocytic lineage, comprising: contacting said cells with antibodies specific for CD34, M-CSFR and CD64; and then flow cytometrically depleting cells that are CD34$^{hi}$M-CSFR$^+$CD64$^-$ wherein a CD34$^{hi}$M-CSFR$^+$CD64$^-$ phenotype indicates granulo-monocytic lineage progenitor cells.

5. The method of any one of claims 2–4 wherein said antibodies specific for CD34 and CD64 are detectably and discriminably labeled.

6. The method of any one of claims 2–4 wherein said antibodies specific for CD34, M-CSFR and CD64 are detectably and discriminably labeled by direct conjugation with a fluorophore.

7. The method of claim 6 wherein said fluorophore is selected from the group consisting of fluorescein isothiocyanate (FITC), allophycocyanin (APC), peridinin chlorophyll protein (Per CP), phycoerythrin (PE) and Cyanine 5 (Cy5).

8. The method of claim 7 wherein said antibody specific for CD34 is conjugated to FITC and said antibody specific for CD64 is conjugated to APC.

* * * * *